(12) United States Patent
Brennan et al.

(10) Patent No.: US 8,685,931 B2
(45) Date of Patent: Apr. 1, 2014

(54) HAIR GROWTH METHODS USING FGFR3 EXTRACELLULAR DOMAINS

(75) Inventors: Thomas Brennan, Saratoga, CA (US); Robert Dean, Alameda, CA (US); W. Michael Kavanaugh, Orinda, CA (US); Janine Powers, Alameda, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 13/515,429

(22) PCT Filed: Dec. 17, 2010

(86) PCT No.: PCT/US2010/061157
§ 371 (c)(1),
(2), (4) Date: Nov. 21, 2012

(87) PCT Pub. No.: WO2011/084711
PCT Pub. Date: Jul. 14, 2011

(65) Prior Publication Data
US 2013/0058928 A1    Mar. 7, 2013

Related U.S. Application Data

(60) Provisional application No. 61/287,690, filed on Dec. 17, 2009.

(51) Int. Cl.
*A61K 38/00*     (2006.01)
*A61P 17/14*     (2006.01)
*A61P 35/00*     (2006.01)
*C07K 14/515*    (2006.01)

(52) U.S. Cl.
USPC ........................ 514/20.7; 514/13.3

(58) Field of Classification Search
None
See application file for complete search history.

(56) References Cited

U.S. PATENT DOCUMENTS

| | | |
|---|---|---|
| 5,229,501 A | 7/1993 | Keifer et al. |
| 5,288,855 A | 2/1994 | Bergonzoni et al. |
| 5,474,914 A | 12/1995 | Spaete |
| 5,486,462 A | 1/1996 | Rutter et al. |
| 5,707,632 A | 1/1998 | Williams et al. |
| 5,750,371 A | 5/1998 | Senoo et al. |
| 5,767,250 A | 6/1998 | Spaete |
| 5,863,888 A | 1/1999 | Dionne et al. |
| 6,255,454 B1 | 7/2001 | Keifer et al. |
| 6,344,546 B1 | 2/2002 | Dionne et al. |
| 6,350,593 B1 | 2/2002 | Williams et al. |
| 6,355,440 B1 | 3/2002 | Williams et al. |
| 6,384,191 B1 | 5/2002 | Williams et al. |
| 6,517,872 B1 | 2/2003 | Yayon et al. |
| 6,656,728 B1 | 12/2003 | Kavanaugh et al. |
| 6,844,168 B1 | 1/2005 | Keifer et al. |
| 7,045,550 B2 | 5/2006 | Fahl et al. |
| 7,135,311 B1 | 11/2006 | David et al. |
| 7,297,493 B2 | 11/2007 | Lorenzi et al. |
| 7,297,774 B2 | 11/2007 | Ullrich et al. |
| 7,306,789 B2 | 12/2007 | Doherty et al. |
| 7,335,641 B2 | 2/2008 | Kim et al. |
| 7,388,029 B2 | 6/2008 | DeLong et al. |
| 7,485,618 B2 | 2/2009 | Day et al. |
| 7,524,505 B2 | 4/2009 | Lin et al. |
| 7,589,060 B2 | 9/2009 | Imamura et al. |
| 7,645,609 B2 | 1/2010 | Follstad |
| 7,678,890 B2 | 3/2010 | Bosch et al. |
| 7,982,014 B2 | 7/2011 | Williams et al. |
| 8,119,770 B2 | 2/2012 | Blanche et al. |
| 8,173,134 B2 | 5/2012 | Bosch et al. |
| 8,338,569 B2 | 12/2012 | Marshall et al. |
| 2004/0063910 A1 | 4/2004 | Kavanaugh et al. |
| 2004/0115768 A1 | 6/2004 | Follstad |
| 2005/0187150 A1 | 8/2005 | Mohammadi et al. |
| 2006/0024705 A1 | 2/2006 | Centola et al. |
| 2006/0234347 A1 | 10/2006 | Harding et al. |
| 2006/0286102 A1 | 12/2006 | Jin et al. |
| 2007/0248604 A1 | 10/2007 | Desnoyers et al. |
| 2007/0248605 A1 | 10/2007 | Hestir et al. |
| 2008/0171689 A1 | 7/2008 | Williams et al. |
| 2012/0128672 A1 | 5/2012 | Keer |
| 2012/0183541 A1 | 7/2012 | Brennan et al. |
| 2012/0237511 A1 | 9/2012 | Long et al. |
| 2012/0251538 A1 | 10/2012 | Harding et al. |
| 2012/0301921 A1 | 11/2012 | Williams et al. |
| 2013/0004492 A1 | 1/2013 | Marshall et al. |

FOREIGN PATENT DOCUMENTS

| | | |
|---|---|---|
| EP | 0455422 A2 | 11/1991 |
| EP | 0545343 | 6/1993 |
| EP | 1910542 | 2/2009 |
| EP | 2083081 | 7/2009 |
| EP | 2127674 | 12/2009 |
| WO | 91/00916 | 1/1991 |
| WO | 91/11459 | 8/1991 |
| WO | 2004/006949 | 1/2004 |
| WO | 2004/110487 | 12/2004 |
| WO | 2005/113596 | 12/2005 |

(Continued)

OTHER PUBLICATIONS

Bodo et al., "Dissecting the Impact of Chemotherapy on the Human Hair Follicle," Am J Pathol, 2007, 171 (4):1153-1167.

(Continued)

*Primary Examiner* — Robert Landsman
(74) *Attorney, Agent, or Firm* — Casimir Jones, S.C.

(57) ABSTRACT

The present invention relates to a method of promoting hair growth comprising administering a fibroblast growth factor receptor 3 (FGFR3) extracellular domain (ECD), including native FGFR3 ECDs, variants, fragments, and fusion molecules, to a subject in an amount sufficient to promote hair growth.

41 Claims, 5 Drawing Sheets

(56) References Cited

FOREIGN PATENT DOCUMENTS

| WO | 2005/115363 | 12/2005 |
|---|---|---|
| WO | 2006/081430 | 8/2006 |
| WO | 2006/113277 | 10/2006 |
| WO | 2007/014123 | 2/2007 |
| WO | 2007/059574 | 5/2007 |
| WO | 2007/134210 | 11/2007 |
| WO | 2008/065543 | 6/2008 |
| WO | 2008/118877 | 10/2008 |
| WO | 2011/034940 | 3/2011 |
| WO | 2011/060333 | 5/2011 |

OTHER PUBLICATIONS

Botchkarev, "Stress and the Hair Follicle: Exploring the Connections," Am J Pathol, 2003, 162(3):709-712.
Botchkarev et al., "Neurotrophins in Skin Biology and Pathology," J Invenst Dermatol, 2006, 126:1719-1727.
Fessing et al., "Involvement of the Edar Signaling in the Control of Hair Follicle Involution (Catagen)," Am J Path, 2006, 169(6):2075-2084.
Gilhar et al., "Lymphocytes, neuropeptides, and genes involoved in alopecia areata," J Clinical Invenst, 2007, 117 (8):2019-2027.
Harrison et al., "Diffuse hair loss: Its triggers and management," Cleveland Clinical J Med, 2009, 76(6):391-367.
Du Cros, "Fibroblast Growth Factor and Epidermal Growth Factor in Hair Development," J. Investig. Dermatol., 1993, 101:106S-1113S.
Kawano et al., "Comprehensive Analysis of FGF and FGFR Expression in Skin: FGF18 Is Highly Expressed in Hair Follicles and Capable of Inducing Anagen from Telogen Stage Hair Follicles," J Invest Dermatol 124:877-885, 2005.
Ito et al., Maintenance of Hir Follicle Immune Privilege is Linked to Prevention of NK Cell Attack., J. Invenst Dermatol, 2008, 128:1196-1206.
Lin et al., "Cicadian Clock Genes Contribute to the Regulation of Hair Follicle Cycling," PLoS Genet., 2009, 5(7): e1000573, 14 pages.
Novack et al., "Alpecia: Possible Causes and Treatments, Particularly in Captive Nonhuman Primates," Comparative Medicine, 2009, 59(1):18-29.
Peters et al., "Probing the Effects of Stress Mediators on the Human Hair Follicle," Am. J. Pathol., 2007, 171 (6):1872-1886.
Plikus et al., "Complex Hair Cycle Domain Patters and Regenerative Hair Waves in Lving Rodents," J. Invest. Dermatol, 2008, 128:1071-1080.
Porter, "Mouse models for human hair loss disorders," J. Anat., 2003, 202:125-131.
Rosenquist et al., "Fibroblast Growth Factor Signalling in the Hair Growth Cycle: Expression of the Fibroblast Growth Factor Receptor and Lignan Genes in the Murine Hair Follicle," Developmental Dynamics, 1996, 205:379-386.
Schneider et al., "Betacellulin Regulates Hair Follicle Development and Hair Cycle Induction and Enhances Angiogenesis in Wounded Skin," J. Invest. Dermatol., 2008, 128:1256-1265.
Sharov et al., "Fas Signaling is Involved in the Control of Hair Follicle Response to Chemotherapy," Cancer Res., 2004, 64:6266-6270.
Sharov et al., "Changes in Different Melanocyte Populations During Hair Follicle Involution (Catagen)," J. Inventst. Dermatol., 2005, 125:1259-1267.
Sharov et al., "Bone morphogenetic protein (BMP) signaling controls hair pigmentation by means of cross-talk with the melanocortin receptor-1 pathway," PNAS, 2005, 102(1):93-98.
Sharov et al., "Bone morphogenetic protein signaling regulates the size of hair follicles and modulates the expression of cell cycle-associated genes," PNAS, 2006, 103(48):18166-18171.
Siebenhaar et al., "Substancde P as an Immunomodulatory Neuropeptide in a Mouse Model for Autoimmune Hair Loss Alopecia Areata," J. Invest. Dermatol., 2007, 127:1489-1497.
Slominski et al., "Skin as an endocrine organ: implications for its function," Drug Discov. Today Dis. Mech., 2008, 5 (2):137-144.

Akimoto et al., "Fibroblast growth factor 2 promotes microvessel formation from mouse embryonic aorta" Am. J. Physiol. Cell Physiol., vol. 284, No. 2, 2003, pp. C371-C377.
Anderson et al., "Apert syndrome mutations in fibroblast growth factor receptor 2 exhibit increased affinity for FGF ligand" Human Molecular Genetics, vol. 7, No. 9, 1998, pp. 1475-1483.
Andre et al., "Molecular Characterization of Breast Cancer with High-Resolution Oligonucleotide Comparative Genomic Hybridization Array," Clin Cancer Res, 2009, 15(2): 441-451.
Auguste et al., "Inhibition of fibroblast growth factor-fibroblast growth factor receptor activity in glioma cells impedes tumor growth by both angiogenesis-dependent and -independent mechanisms" Cancer Research, vol. 61, Feb. 15, 2001, pp. 1717-1726.
Baker et al., "Metabolic control of recombinant protein N-glycan processing in NSO and CHO cells" Biotechnology and Bioengineering, vol. 73, No. 3, May 5, 2001, pp. 188-202.
Ballinger et al., "Semirational design of a potent, artificial agonist of fibroblast growth factor receptors" Nature Biotechnology, vol. 17, Dec. 1999, pp. 1199-1204.
Bansal et al., "The Molecular Biology of Endometrial Cancers and the Implications for Pathogenesis, Classification, and Targeted Therapies," Cancer Control, 2009, 16(1):8-13.
Bass et al., "SOX2 Is an Amplified Lineage Survival Oncogene in Lung and Esophageal Squamous Cell Carcinomas," Nat. Genet., 2009, 41(11): 1238-1242, including supplemental information (15 pages).
Beroukhim et al., "The landscape of somatic copy—number alteration across human cancers," Nature, 2010, 463: 899-905.
Bjornsson et al., Pharmacokinetics of Heparin. II. Studies of Time Dependence in Rats, the Journal of Pharmacology and Experimental Therapeutics, vol. 210, No. 2, Apr. 1979, pp. 243-246.
Byron and Pollock, "FGFR2 as a molecular target in endometrial cancer," Future Oncol, 2009, 5(1):27-32.
Byron et al., "Inhibition of Activated Fibroblast Growth Factor Receptor 2 in Endometrial Cancer Cells Induces Cell Death Despite PTEN Abrogation," Cancer Res, 2008, 68(17):6902-6907.
Byron et al., "FGFR2 mutations are rare across histologic subtypes of ovarian cancer," Gynecologic Oncology, 2010, 117(1):125-129.
Celli et al., "Soluble dominant-negative receptor uncovers essential roles for fibroblast growth factors in multi-organ induction and patterning" The EMBO Journal, vol. 17, No. 6, Mar. 16, 1998, pp. 1642-1655.
Chellaiah et al., "Mapping ligand binding domains in chimeric fibroblast growth factor receptor molecules" J. Biol. Chem., vol. 274, No. 49, Dec. 3, 1999, pp. 34785-34794.
Cheon et al., "High-affinity binding sites for related fibroblast growth factor ligands reside within different receptor immunoglobulin-like domains" Proc. Natl. Acad. Sci., vol. 91, Feb. 1994, pp. 989-993.
Choo et al., SPdb—a Signal Peptide Database, BMC Bioinformatics, vol. 6, No. 249, Oct. 2005, pp. 1-8.
Compagni et al., "Fibroblast growth factors are required for efficient tumor angiogenesis" Cancer Research, vol. 60, Dec. 15, 2000, pp. 7163-7169.
Coughlin et al., "Acidic and basic fibroblast growth factors stimulate tyrosine kinase activity in vivo" J. Biol. Chem., vol. 263, No. 2, Jan. 15, 1988, pp. 988-993.
Courjal et al., "Comparative Genomic Hybridization Analysis of Breast Tumors with Predetermined Profiles of DNA Amplification," Cancer Res. 1997, 57(19):4368-77.
Cuny et al., "Relating genotype and phenotype in breast cancer: an analysis of the prognostic significance of amplification at eight different genes or loci and of p53 mutations," Cancer Res. 2000; 60(4):1077-83.
Dutt et al., "Drug-sensitive FGFR2 mutations in endometrial carcinoma," PNAS, 2008, 105(25):8713-8717.
Dutt et al., "Inhibitor-Sensitive FGFR1 Amplification in Human Non-Small Cell Lung Cancer," 2011, PLoS One, 6(6):e20351, 10 pages.
Elbauomy Elsheikh et al., "FGFR1 amplification in breast carcinomas: a chromogenic in situ hybridisation analysis," Breast Cancer Research 2007, 9:R23, 12 pages.

(56) References Cited

OTHER PUBLICATIONS

Ezzat et al., "A soluble dominant negative fibroblast growth factor receptor 4 isoform in human MCF-7 breast cancer cells" Biochem. Biophys. Res. Comm., vol. 287, No. 1, 2001, pp. 60-65.
Feige et al., "Glycosylation of the basic fibroblast growth factor receptor" J. Biol. Chem., vol. 263, No. 28, Oct. 5, 1988, pp. 14023-14029.
Gatius et al., "FGFR2 alterations in endometrial carcinoma," Modern Pathology, 2011, 24:1500-1510.
Gelsi-Boyer et al., "Comprehensive Profiling of 8p11-12 Amplification in Breast Cancer," Mol Cancer Res 2005;3 (12): 655-667.
Genbank Accession No. X76885, 1994, 2 pages.
Genbank Accession No. Q90330, Nov. 1, 1996, 6 pages.
Gowardhan et al., "Evaluation of the fibroblast growth factor system as a potential target for therapy in human prostate cancer" British Journal of Cancer, vol. 92, Jan. 18, 2005, pp. 320-327.
Grossman et al., "Expression of human thyrotropin in cell lines with different glycosylation patterns combined with mutagenesis of specific glycosylation sites" J. Biol. Chem., vol. 270, No. 49, Dec. 8, 1995, pp. 29378-29385.
Guillonneau et al., "Fibroblast growth factor (FGF) soluble receptor 1 acts as a natural inhibitor of FGF2 neurotrophic activity during retinal degeneration" Molecular Biology of the Cell, vol. 9, Oct. 1998, pp. 2785-2802.
Hanneken et al., "Identification of soluble forms of the fibroblast growth factor receptor in blood" Proc. Natl. Acad. Sci., vol. 91, Sep. 1994, pp. 9170-9174.
Hanneken et al., "Soluble forms of the high-affinity fibroblast growth factor receptor in human vitreous fluid" Investigative Opthalmology & Visual Science, vol. 36, No. 6, May 1995, pp. 1192-1196.
Hanneken et al., "Structural characterization of the circulating soluble FGF receptors reveals multiple isoforms generated by secretion and ectodomain shedding" FEBS Letters, vol. 489, 2001, pp. 176-181.
Harding et al., "Role of VEGF, PDGF and FGF in glioblastoma progression as determined by soluble decoy receptor expression in preclinical models" Cell Genesys, Inc., Abstract No. 3030, presented at the AACR Annual Meeting, Apr. 16-20, 2005, 1 page.
Harding et al., "Preclinical Efficacy of FP-1039 (FGFR1:Fc) in Endometrical Carcinoma Models with Activating Mutations in FGFR2," AACR 101st Annual Meeting Poster (Apr. 17-21, 2010).
Ibrahimi et al., "Structural basis for fibroblast growth factor receptor 2 activation in Apert syndrome," PNAS, 2001, 98 (13):7182-7187.
Ibrahimi et al., "Biochemical analysis of pathogenic ligand-dependent FGFR2 mutations suggests distinct pathophysiological mechanisms for craniofacial, and limb abnormalities," Human Molecular Genetics, 2004, 13 (19):2313-2324.
Ibrahimi et al., "Proline to arginine mutations in FGF receptors 1 and 3 result in Pfeiffer and Muenke craniosynostosis syndromes through enhancement of FGF binding affinity," Hum. Mol. Genet., 13: 69-78 (2004).
Ibrahimi et al., "Analysis of Mutations in Fibroblast Growth Factor (FGF) and a Pathogenic Mutation in FGF Receptor (FGFR) Provides Direct Evidence for the Symmetric Two-End Model for FGFR Dimerization," Mol. Cell. Biol., 25(2): 671-684 (2005).
Johnson et al., "Diverse forms of a receptor for acidic and basic fibroblast growth factors" Molecular and Cellular Biology, vol. 10, No. 9, Sep. 1990, pp. 4728-4736.
Johnson et al, "The human fibroblast growth factor receptor genes: a common structural arrangement underlies the mechanisms for generating receptor forms that differ in their third immunoglobulin domain" Molecular and Cellular Biology, vol. 11, No. 9, Sep. 1991, pp. 4627-4634.
Kan et al., "Divalent cations and heparin-heparan sulfate cooperate to control assembly and activity of the fibroblast growth factor receptor complex" J. Biol. Chem., vol. 271, No. 42, Oct. 18, 1996, pp. 26143-26148.
Katoh, "Cancer genomics and genetics of FGFR2 (Review)," International Journal of Oncology, 2008, 33:233-237.

Katoh, "FGFR2 Abnormalities Underlie a Spectrum of Bone, Skin, and Cancer Pathologies," Journal of Investigative Dermatology, 2009, 129:1861-1867.
Kaufman et al., "Characterization of ligand binding to immobilized biotinylated extracellular domains of three growth factor receptors" Anal. Biochem, vol. 211, No. 2, Jun. 1993, pp. 261-266.
Keer et al., "Enrolling a Rare Patient Population: Establishing Proof of Concept for FP-1039, an FGF 'Trap,' in Endometrial Cancer Patients with the S252W FGFR2 Mutation," American Society of Clinical Oncology 2010, Annual Meeting, Jun. 4-8, 2010, Chicago, IL.
Keifer et al., "Molecular cloning of a human basic fibroblast growth factor receptor cDNA and expression of a biologically active extracellular domain in a baculovirus system" Growth Factors, vol. 5, 1991, pp. 115-127.
Tucker et al., "A novel approach for inhibiting growth factor signalling in murine tooth development" Eur. J. Oral Sci., vol. 106 (suppl. 1), 1998, pp. 122-125.
Tuominen et al., "Expression and glycosylation studies of human FGF Receptor 4" Protein Expression and Purification, vol. 21, Mar. 2001, pp. 275-285.
Turner et al., "FGFR1 Amplification Drives Endocrine Therapy Resistance and Is a Therapeutic Target in Breast Cancer," Cancer Research, 2010, 70(5): 2085-2094.
Ueno et al., "A truncated form of fibroblast growth factor receptor 1 inhibits signal transduction by multiple types of fibroblast growth factor receptor" J. Biol. Chem., vol. 267, No. 3, Jan. 25, 1992, pp. 1470-1476.
Van Den Nieuwenhof et al., "Recombinant glycodelin carrying the same type of glycan structures as contraceptive glycodelin-A can be produced in human kidney 293 cells but not in Chinese hamster ovary cells" Eur. J. Biochem., vol. 267, Aug. 2000, pp. 4753-4762.
Voortman et al., "Array comparative genomic hybridization-based characterization of genetic alterations in pulmonary neuroendocrine tumors," 2010, PNAS, 107(29): 13040-13045.
Wagner et al., "Suppression of fibroblast growth factor receptor signaling inhibits pancreatic cancer growth in vitro and in vivo" Gastroenterology, vol. 114, Apr. 1998, pp. 798-807.
Wang et al., "Alternately Spliced NH2-terminal Immunoglobulin-like Loop I in the Ectodomain of the Fibroblast Growth Factor (FGF) Receptor 1 Lowers Affinity for both Heparin and FGF-1," J. Biol. Chem, 1995, 270(17): 10231-10235.
Wang et al., "Purification and characterization of a functional soluble fibroblast growth factor receptor 1" Biochem. Biophys. Res. Comm., vol. 203, No. 3, Sep. 30, 1994, pp. 1781-1788.
Wang et al., "A natural kinase-deficient variant of fibroblast growth factor receptor 1" Biochemistry, Vo. 35, 1996, pp. 10134-10142.
Weiss et al., "Frequent and Focal FGFR1 Amplification Associates with Therapeutically Tractable FGFR1 Dependency in Squamous Cell Lung Cancer," Science Trans. Med., 2010, 2(62): 62ra93, 8 pages.
Wells, "Additivity of Mutational Effects in Proteins," Biochemistry, 1990, 29(37):8509-8517.
Werner et al., "Differential splicing in the extracellular region of fibroblast growth factor receptor 1 generates receptor variants with different ligand-binding specificities" Molecular and Cellular Biology, vol. 12, No. 1, Jan. 1992, pp. 82-88.
Williams et al., "Activation of the FGF receptor underlies neurite outgrowth stimulated by L1, N-CAM, and N-Cadherin" Neuron, vol. 13, Sep. 1994, pp. 583-594.
Ye et al., "FGF and Shh signals control dopaminergic and serotonergic cell fate in the anterior neural plate" Cell, vol. 93, May 29, 1998, pp. 755-766.
Yu et al., "Loss of fibroblast growth factor receptor 2 ligand-binding specificity in Apert syndrome," PNAS, 2000, 97 (26):14536-14541.
Zhang et al., Receptor Specificity of the Fibroblast Growth Factor Family: The Complete Mammalian FGF Family, The Journal of Biological Chemistry, vol. 281, No. 23, Jun. 9, 2006, pp. 15694-15700.
Zhang et al., "FP-1039 (FGFR1:Fc), A Soluble FGFR1 Receptor Antagonis, Inhibits Tumor Growth and Angiogenesis," AACR-NCI-EORTC International Conference, Oct. 22-26, 2007, San Francisco, CA.

(56) References Cited

OTHER PUBLICATIONS

Zheng et al. "Enhanced efficacy in anti-tumour activity by combined therapy of recombinant FGFR-1 related angiogenesis and low-dose cytotoxic agent," European Journal of Cancer, vol. 43, No. 14, Sep. 14, 2007, pp. 2134-2139.
File History for U.S. Appl. No. 11/791,889, filed May 30, 2007.
File history for U.S. Appl. No. 12/535,479, filed Aug. 4, 2009.
File History for U.S. Appl. No. 12/652,720, filed Jan. 5, 2010.
File History for U.S. Appl. No. 13/157,712, filed Jun. 10, 2011.
File history for U.S. Appl. No. 13/227,398, filed Sep. 7, 2011.
File History for U.S. Appl. No. 13/296,161, filed Nov. 14, 2011.
File History for U.S. Appl. No. 13/296,168, filed Nov. 14, 2011.
File History for U.S. Appl. No. 13/496,182, filed Mar. 14, 2012.
File History for U.S. Appl. No. 13/438,638, filed Apr. 3, 2012.
File History for U.S. Appl. No. 13/509,068, filed Jun. 13, 2012.
File History for U.S. Appl. No. 13/612,044, filed Sep. 12, 2012.
File History for U.S. Appl. No. 13/675,255, filed Nov. 13, 2012.
International Search Report and Written Opinion mailed Mar. 8, 2012 for PCT/US2009/052704, filed Aug. 4, 2009.
International Search Report and Written Opinion of the International Searching Authority, mailed Sep. 18, 2007, for International Application No. PCT/US2006/028597, 23 pages.
International Preliminary Report on Patentability, mailed Jan. 22, 2008, for International Application No. PCT/US2006/028597, 14 pages.
International Search Report and Written Opinion, mailed Jan. 24, 2011, for International Patent Application PCT/US2010/048957, 10 pages.
International Search Report and Written Opinion, mailed Feb. 4, 2011, for International Patent Application PCT/US2010/056627, 15 pages.
International Search Report and Written Opinion of the International Searching Authority, mailed Feb. 3, 2012, for International Application No. PCT/US2010/061157, 12 pages.
International Search Report and Written Opinion of the International Searching Authority, mailed Jan. 31, 2012, for International Application No. PCT/US2011/060661, 16 pages.
International Search Report and Written Opinion of the International Searching Authority, mailed Apr. 12, 2012, for International Application No. PCT/US2011/060666, 20 pages.
European Search Report, mailed Jun. 5, 2009, in European Application No. 09075061.3, 2 pages.
Kleeff et al., "Adenovirus-mediated transfer of a truncated fibroblast growth factor (FGF) type I receptor blocks FGF-2 signaling in multiple pancreatic cancer cell lines" Pancreas, vol. 28, No. 1, Jan. 2004, pp. 25-30.
Kwabi-Addo et al., "The role of fibroblast growth factors and their receptors in prostate cancer" Endocrine-Related Cancer, vol. 11, No. 4, Dec. 2004, pp. 709-724.
Lazar et al., "Transforming Growth Factor alpha: Mutation of Aspartic Acid 47 and Leucine 48 Results Different Biological Activities," Mol Cell Biol, 1988, 8(3):1247-1252.
Lee et al., "Purification and complementary DNA cloning of a receptor for basic fibroblast growth factor" Science, vol. 245, No. 4913, Jul. 7, 1989, pp. 57-60.
Lee et al., "Molecular profiles of EGFR, K-ras, c-met, and FGFR in pulmonary pleomorphic carcinoma, a rare lung malignancy," J. Cancer Res. Clin. Oncol., May 28, 2011, 9 pages.
Levi et al., "Matrix metalloproteinase 2 releases active soluble ectodomain of fibroblast growth factor receptor 1", XP-002413740, Proc. Natl. Acad. Sci., USA, vol. 93, pp. 7069-7074, (Jul. 1996).
Li et al., "Cell transformation by fibroblast growth factors can be suppressed by truncated fibroblast growth factor receptors" Molecular and Cellular Biology, vol. 14, No. 11, Nov. 1994, pp. 7660-7669.
Liu et al, "Utilization of Unlabeled Probes for the Detection of Fibroblast Growth Factor Receptor 2 Exons 7 and 12 Mutations in Endometrial Carcinoma," Appl Immunohistochem Mol Morphol, 2011, 19(4):341-346.

Liuzzo et al., "Human leukemia cell lines bind basic fibroblast growth factor (FGF) on FGF receptors and heparin sulfates: downmodulation of FGF receptors by phorbol ester" Blood, vol. 87, No. 1, Jan. 1, 1996, pp. 245-255.
Long et al. "Abstract #2789: Antitumor efficacy of FP-1039, a soluble FGF receptor 1:Fc conjugate, as a single agent or in combination with anticancer drugs," Proceedings of the American Association for Cancer Research, Apr. 18-22, 2009 Denver, CO.
Long et al. "Preclinical antitumor efficacy of FP-1039, a soluble FGF receptor 1:Fc conjugate, as a single agent or in combination with anticancer drugs," Proceedings of the American association for Cancer Research, Apr. 17-22, 2009 Denver, CO.
Loo et al., "Production and characterization of the extracellular domain of recombinant human fibroblast growth factor receptor 4," Intl. J. Biochem. Cell Biol., 2000, 32: 489-497.
Lopez et al., "A novel type I fibroblast growth factor receptor activates mitogenic signaling in the absence of detectable tyrosine phosphorylation of FRS2" J. Biol. Chem., vol. 275, No. 21, May 26, 2000, pp. 15933-15939.
Lundin et al., "Selectively desulfated heparin inhibits fibroblast growth factor-induced mitogenicity and angiogenesis" J. Biol. Chem., vol. 275, No. 32, Aug. 11, 2000, pp. 24653-24660.
Mansukhani et al., "A murine fibroblast growth factor (FGF) receptor expressed in CHO cells is activated by basic FGF and Kaposi FGF" Proc. Natl. Acad. Sci., vol. 87, Jun. 1990, pp. 4378-4382.
Marics et al., "FGFR4 signaling is a necessary step in limb muscle differentiation," Development, 2002, 129:4559-4569.
Marshall et al., "Fibroblast Growth Factor Receptors Are Components of Autocrine Signaling Networks in Head and Neck Squamous Cell Carcinoma Cells," 2011, 17(15): 5016-5025.
Meijer et al., Fibroblast Growth Factor Receptor 4 Predicts Failure on Tamoxifen Therapy in Patients with Recurrent Breast Cancer, Endocrine-Related Cancer, vol. 15, 2008, pp. 101-111.
Moloney et al., "Exclusive paternal origin of new mutations in Apert syndrome," Nature Genetics, 1996, 13:48-53.
Ogawa et al., "Anti-tumor angiogenesis therapy using soluble receptors: enhanced inhibition of tumor growth when soluble fibroblast growth factor receptor-1 is used with soluble vascular endothelial growth factor receptor" Cancer Gene Therapy, vol. 9, Aug. 2002, pp. 633-640.
Olsen et al., "Insights into the molecular basis for fibroblast growth factor receptor autoinhibition and ligand-binding promiscuity" Proc. Natl. Acad. Sci., vol. 101, No. 4 Jan. 27, 2004, pp. 935-940.
Ornitz et al., "Heparin is required for cell-free binding of basic fibroblast growth factor to a soluble receptor and for mitogenesis in whole cells" Molecular and Cellular Biology, vol. 12, Jan. 1992, pp. 240-247.
Ornitz et al., "Receptor specificity of the fibroblast growth factor family" J. Biol. Chem., vol. 271, No. 25, Jun. 21, 1996, pp. 15292-15297.
Otto et al., "Sialylated complex-type N-glycans enhance the signaling activity of soluble intercellular adhesion molecule-1 in mouse astrocytes" J. Biol. Chem., vol. 279, No. 34, Aug. 20, 2004, pp. 35201-35209.
Pasquale et al., "Identification of a developmentally regulated protein-tyrosine kinase by using anti-phosphotyrosine antibodies to screen a cDNA expression library" Proc. Natl. Acad. Sci., vol. 86, Jul. 1989, pp. 5449-5453.
Pellegrini et al., "Crystal structure of fibroblast growth factor receptor ectodomain bound to ligand and heparin," Nature, 2000, 407: 1029-1034.
Plotnikov et al., "Structural basis for FGF receptor dimerization and activation" Cell, vol. 98, Sep. 3, 1999, pp. 641-650.
Plotnikov et al., "Crystal structures of two FGF-FGFR complexes reveal the determinants of ligand-receptor specificity" Cell, vol. 101, May 12, 2000, pp. 413-424.
Pollock et al., "Frequent activating FGFR2 mutations in endometrial carcinomas parallel germline mutations associated with craniosynostosis and skeletal dysplasia syndromes," Oncogene, 2007, 26:7158-7162.
Powell et al., "Fibroblast growth factor receptors 1 and 2 interact differently with heparin-heparan sulfate" J. Biol. Chem., vol. 277, No. 32, Aug. 9, 2002, pp. 28554-28563.

(56) References Cited

OTHER PUBLICATIONS

Powers et al., "Fibroblast growth factors, their receptors and signaling", XP-002165147, Endocrine-Related Cancer, 7, pp. 165-197, (2000).
Rang et al, "Cancer chemotherapy," Rang and Dale's Pharmacology, Churchill Linvingston Elsevier, 2008, pp. 718-735.
Reis-Filho et al., "FGFR1Emerges as a PotentialTherapeuticTarget for Lobular Breast Carcinomas," 2006, Clin. Cancer Res. 12(22): 6652-6662.
Robertson et al., "Activating mutations in the extracellular domain of the fibroblast growth factor receptor 2 function by disruption of the disulfide bond in the third immunoglobulin-like domain," Proc. Natl. Acad. Sci., USA, 1998, 95: 4567-4572.
Roghani et al., "Heparin increases the affinity of basic fibroblast growth factor for its receptor but is not required for binding" J. Biol. Chem., vol. 269, No. 6, Feb. 11, 1994, pp. 3976-3984.
Ruta et al., "A novel protein tyrosine kinase gene whose expression is modulated during endothelial cell differentiation" Oncogene, 1988, vol. 3, pp. 9-15.
Sahadevan et al., Selective Over-expression of Fibroblast Growth Factor Receptors I and 4 in Clinical Prostate Cancer, Journal of Pathology, vol. 213, Jul. 2007, pp. 82-90.
Sanchez-Heras et al., "The fibroblast growth factor receptor acid box is essential for interactions with N-cadherin and all of the major isoforms of neural cell adhesion molecules," J Biol Chem, 2006, 281(46):35208-16.
Schlessinger et al., "Crystal Structure of the Ternary FGF-FGFR-Heparin Complex Reveals a Dual Role for Heparin in FGFR Binding and Dimerization," Molecular Cell, 2000, 6: 743-750.
Shamim et al., "Sequential roles for Fgf4, En1 and Fgf8 in specification and regionalization of the midbrain" Development, vol. 126, Feb. 1999, pp. 945-959.
Smith et al., "The asparagine-linked oligosaccharides on tissue factor pathway inhibitor terminate with SO4-4GalNAcβ1,4GlcNAcβ1,2Manα" J. Biol. Chem., vol. 267, No. 27, Sep. 25, 1992, pp. 19140-19146.
St. Bernard et al., "Fibroblast growth factor receptors as molecular targets in thyroid carcinoma" Endocrinology, vol. 146, No. 3, 2005, pp. 1145-1153.
St. Bernard et al., "Fibroblast growth factor receptors as molecular targets in thyroid carcinoma" Endocrinology, vol. 10, Nov. 24, 2004, pp. 1-26 and 6 pgs. figures.
Stauber et al., "Structural interaction of fibroblast growth factor receptor with its ligands," Proc. Natl. Acad. Sci., USA, 2000, 97(1): 49-54.
Sugiura et al., "Co-expression of aFGF and FGFR-1 is predictive of a poor prognosis in patients with esophageal squamous cell carcinoma," Oncology Reports, 2007, 17: 557-564.
Tolcher et al., "Preliminary Results of a Phase 1 Study of FP-1039 (FGFR1:Fc), A Novel Antogonist of Multiple Fibroblast Growth Factor (FGF) Ligands, in Patients With Advanced Malignancies," 2009 AACR-EORTC-NCI Molecular Targets and Cancer Therapeutics Conference Poster (Nov. 15-18, 2009).
Tolcher et al., "Preliminary Results of a Dose Escalation Study of the Fibroblast Growth Factor (FGF) "trap" FP-1039 (FGFR1:Fc) in Patients With Advanced Malignancies," 22nd EORTC-NCI-AACR Symposium on Molecular Targets and Cancer Therapeutics Poster (Nov. 16-19, 2010).
Tolcher et al., "Preliminary results of a dose escalation study of the Fibroblast Growth Factor (FGF) "trap" FP-1039 (FGFR1:Fc) in patients with advanced malignancies," European Journal of Cancer, Supplement, 8(7): 121, Abstract No. 381 (Nov. 18, 2010).
Tomlinson et al., "Alternative splicing of fibroblast growth factor receptor 3 produces a secreted isoform that inhibits fibroblast growth factor-induced proliferation and is repressed in urothelial carcinoma cell lines" Cancer Research, vol. 65, No. 22, Nov. 15, 2005, pp. 10441-10449.
Trueb et al., "Characterization of FGFRL1, a novel fibroblast growth factor (FGF) receptor preferentially expressed in skeletal tissues" J. Biol. Chem., vol. 278, No. 36, Sep. 5, 2003, pp. 33857-33865.
European Search Report and Opinion for EP10842665, dated Dec. 3, 2013, 7 pages.

FIG. 2

Ig domain III of FGFRs

```
FGFR3 IIIa  LKHVEVNGSKVGPDGTPYVTVLK-----------------LKHVEVNGSKVGPDGTPYVTVLK-------------------------
FGFR3 IIIb  LKHVEVNGSKVGPDGTPYVTVLKSWISESVEADVRLR-LANVSERDGGEYLCRATNFIGV
FGFR3 IIIc  LKHVEVNGSKVGPDGTPYVTVLKTAGANTTDKELEVLSLHNVTFEDAGEYTCLAGNSIGF
FGFR1 IIIb  LKHIEVNGSKIGPDNLPYVQILKHSGINSSD--AEVLTLFNVTEAQSGEYVCKVSNYIGE
FGFR1 IIIc  LKHIEVNGSKIGPDNLPYVQILKTAGVNTTDKEMEVLHLRNVSFEDAGEYTCLAGNSIGL
FGFR2 IIIb  IKHVEKNGSKYGPDGLPYLKVLKHSGINSSNAEVLALFN--VTEADAGEYICKVSNYIGQ
FGFR2 IIIc  IKHVEKNGSKYGPDGLPYLKVLKAAGVNTTDKEIEVLYIRNVTFEDAGEYTCLAGNSIGI
FGFR4       LKHIVINGSSFGADGFPYVQVLKTADINSSE--VEVLYLRNVSAEDAGEYTCLAGNSIGL

FGFR3 IIIa  --------------------------------------------
FGFR3 IIIb  AEKAFWLSVHGPRAAEEELVEADEAGSVYAG
FGFR3 IIIc  SHHSAWLTVLP----AEEELVEADEAGSVYAG
FGFR1 IIIb  ANQSAMLTVTRPVAKALEERPAVMTSPLYLE
FGFR1 IIIc  SHHSAMLTVL-----EALEERPAVMTSPLYLE
FGFR2 IIIb  ANQSAMLTVLPK-QQAPGREKEITASPDYLE
FGFR2 IIIc  SFHSAMLTVLP-----APGREKEITASPDYLE
FGFR4       SYQSAMLTVLP----EEDPTWTAAAPEARYTD
```

FIG. 3A  14 days Post Dose
Vehicle
FGFR2-Fc
FGFR3-Fc
ABMut1
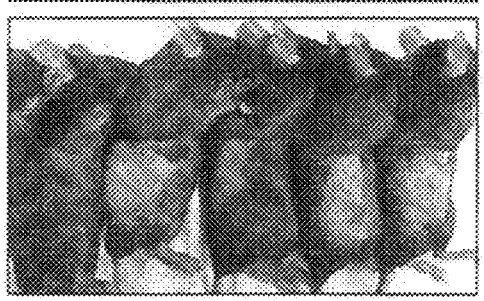

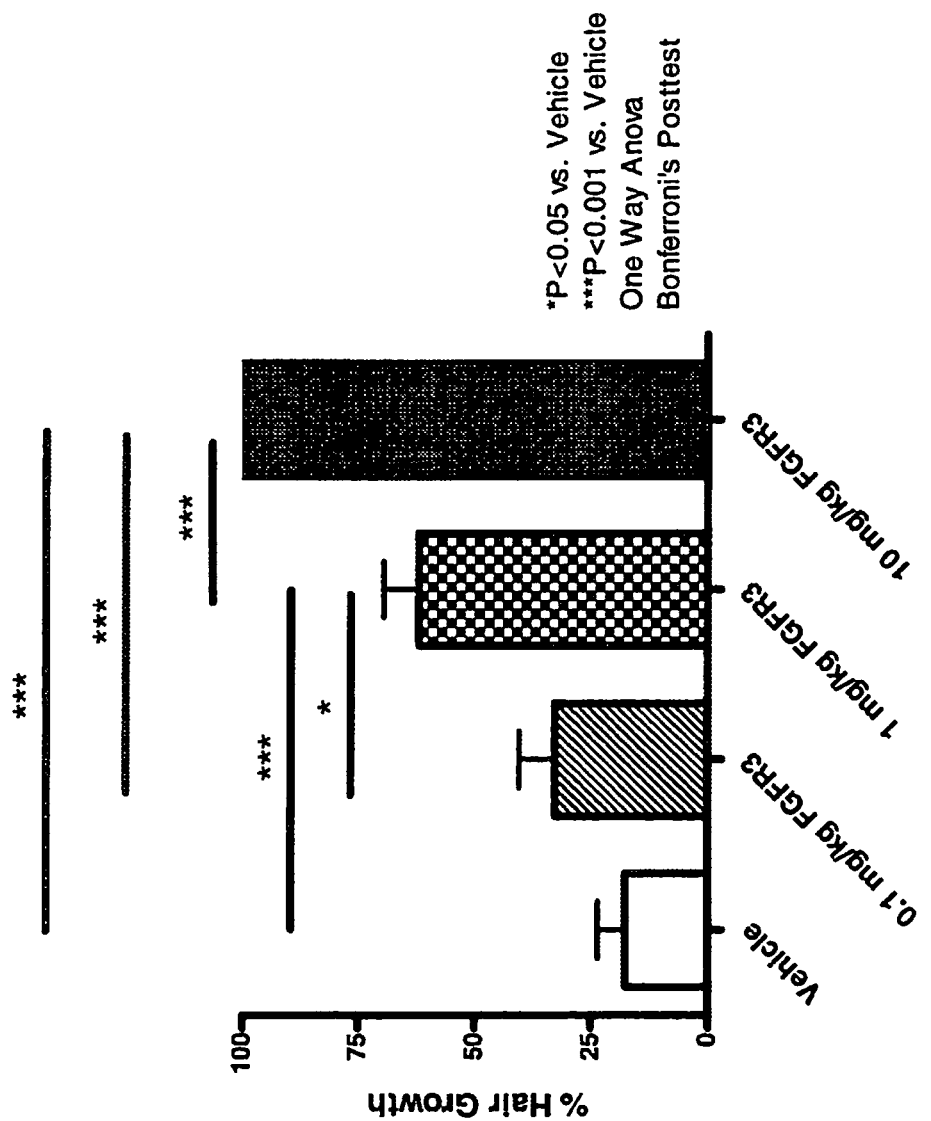

SEQUENCE LISTING

<160> NUMBER OF SEQ ID NOS: 57

<210> SEQ ID NO 1
<211> LENGTH: 784
<212> TYPE: PRT
<213> ORGANISM: Homo sapiens

<400> SEQUENCE: 1

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly

```
                  20                  25                  30
Asp Ala Val Glu Leu Ser Cys Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
    290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Tyr Ala
            340                 345                 350

Gly Ile Leu Ser Tyr Gly Val Gly Phe Phe Leu Phe Ile Leu Val Val
        355                 360                 365

Ala Ala Val Thr Leu Cys Arg Leu Arg Ser Pro Pro Lys Lys Gly Leu
    370                 375                 380

Gly Ser Pro Thr Val His Lys Ile Ser Arg Phe Pro Leu Lys Arg Gln
385                 390                 395                 400

Val Ser Leu Glu Ser Asn Ala Ser Met Ser Ser Asn Thr Pro Leu Val
                405                 410                 415

Arg Ile Ala Arg Leu Ser Ser Gly Glu Gly Pro Thr Leu Ala Asn Val
            420                 425                 430

Ser Glu Leu Glu Leu Pro Ala Asp Pro Lys Trp Glu Leu Ser Arg Ala
        435                 440                 445
```

```
Arg Leu Thr Leu Gly Lys Pro Leu Gly Glu Gly Cys Phe Gly Gln Val
            450                 455                 460

Val Met Ala Glu Ala Ile Gly Ile Asp Lys Asp Arg Ala Ala Lys Pro
465                 470                 475                 480

Val Thr Val Ala Val Lys Met Leu Lys Asp Asp Ala Thr Asp Lys Asp
                485                 490                 495

Leu Ser Asp Leu Val Ser Glu Met Glu Met Met Lys Met Ile Gly Lys
            500                 505                 510

His Lys Asn Ile Ile Asn Leu Leu Gly Ala Cys Thr Gln Gly Gly Pro
        515                 520                 525

Leu Tyr Val Leu Val Glu Tyr Ala Ala Lys Gly Asn Leu Arg Glu Phe
    530                 535                 540

Leu Arg Ala Arg Arg Pro Pro Gly Leu Asp Tyr Ser Phe Asp Thr Cys
545                 550                 555                 560

Lys Pro Pro Glu Glu Gln Leu Thr Phe Lys Asp Leu Val Ser Cys Ala
                565                 570                 575

Tyr Gln Val Ala Arg Gly Met Glu Tyr Leu Ala Ser Gln Lys Cys Ile
            580                 585                 590

His Arg Asp Leu Ala Ala Arg Asn Val Leu Val Thr Glu Asp Asn Val
        595                 600                 605

Met Lys Ile Ala Asp Phe Gly Leu Ala Arg Asp Val His Asn Leu Asp
    610                 615                 620

Tyr Tyr Lys Lys Thr Thr Asn Gly Arg Leu Pro Val Lys Trp Met Ala
625                 630                 635                 640

Pro Glu Ala Leu Phe Asp Arg Val Tyr Thr His Gln Ser Asp Val Trp
                645                 650                 655

Ser Phe Gly Val Leu Leu Trp Glu Ile Phe Thr Leu Gly Gly Ser Pro
            660                 665                 670

Tyr Pro Gly Ile Pro Val Glu Glu Leu Phe Lys Leu Leu Lys Glu Gly
        675                 680                 685

His Arg Met Asp Lys Pro Ala Asn Cys Thr His Asp Leu Tyr Met Ile
    690                 695                 700

Met Arg Glu Cys Trp His Ala Ala Pro Ser Gln Arg Pro Thr Phe Lys
705                 710                 715                 720

Gln Leu Val Glu Asp Leu Asp Arg Val Leu Thr Val Thr Ser Thr Asp
                725                 730                 735

Glu Tyr Leu Asp Leu Ser Ala Pro Phe Glu Gln Tyr Ser Pro Gly Gly
            740                 745                 750

Gln Asp Thr Pro Ser Ser Ser Ser Gly Asp Asp Ser Val Phe Ala
        755                 760                 765

His Asp Leu Leu Pro Pro Ala Pro Pro Ser Ser Gly Gly Ser Arg Thr
    770                 775                 780

<210> SEQ ID NO 2
<211> LENGTH: 672
<212> TYPE: PRT
<213> ORGANISM: Homo sapiens

<400> SEQUENCE: 2

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
            35                  40                  45
```

-continued

```
Pro Thr Val Trp Val Lys Asp Gly Thr Gly Leu Val Pro Ser Glu Arg
 50                  55                  60

Val Leu Val Gly Pro Gln Arg Leu Gln Val Leu Asn Ala Ser His Glu
 65                  70                  75                  80

Asp Ser Gly Ala Tyr Ser Cys Arg Gln Arg Leu Thr Gln Arg Val Leu
                 85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Val Ser Leu Glu Ser Asn Ala Ser Met Ser Ser Asn Thr Pro Leu Val
290                 295                 300

Arg Ile Ala Arg Leu Ser Ser Gly Glu Gly Pro Thr Leu Ala Asn Val
305                 310                 315                 320

Ser Glu Leu Glu Leu Pro Ala Asp Pro Lys Trp Glu Leu Ser Arg Ala
                325                 330                 335

Arg Leu Thr Leu Gly Lys Pro Leu Gly Glu Gly Cys Phe Gly Gln Val
            340                 345                 350

Val Met Ala Glu Ala Ile Gly Ile Asp Lys Asp Arg Ala Ala Lys Pro
        355                 360                 365

Val Thr Val Ala Val Lys Met Leu Lys Asp Asp Ala Thr Asp Lys Asp
370                 375                 380

Leu Ser Asp Leu Val Ser Glu Met Glu Met Met Lys Met Ile Gly Lys
385                 390                 395                 400

His Lys Asn Ile Ile Asn Leu Leu Gly Ala Cys Thr Gln Gly Gly Pro
                405                 410                 415

Leu Tyr Val Leu Val Glu Tyr Ala Ala Lys Gly Asn Leu Arg Glu Phe
            420                 425                 430

Leu Arg Ala Arg Arg Pro Pro Gly Leu Asp Tyr Ser Phe Asp Thr Cys
        435                 440                 445

Lys Pro Pro Glu Glu Gln Leu Thr Phe Lys Asp Leu Val Ser Cys Ala
450                 455                 460

Tyr Gln Val Ala Arg Gly Met Glu Tyr Leu Ala Ser Gln Lys Cys Ile
465                 470                 475                 480
```

His Arg Asp Leu Ala Ala Arg Asn Val Leu Val Thr Glu Asp Asn Val
            485                 490                 495

Met Lys Ile Ala Asp Phe Gly Leu Ala Arg Asp Val His Asn Leu Asp
            500                 505                 510

Tyr Tyr Lys Lys Thr Thr Asn Gly Arg Leu Pro Val Lys Trp Met Ala
            515                 520                 525

Pro Glu Ala Leu Phe Asp Arg Val Tyr Thr His Gln Ser Asp Val Trp
        530                 535                 540

Ser Phe Gly Val Leu Leu Trp Glu Ile Phe Thr Leu Gly Gly Ser Pro
545                 550                 555                 560

Tyr Pro Gly Ile Pro Val Glu Glu Leu Phe Lys Leu Leu Lys Glu Gly
                565                 570                 575

His Arg Met Asp Lys Pro Ala Asn Cys Thr His Asp Leu Tyr Met Ile
            580                 585                 590

Met Arg Glu Cys Trp His Ala Ala Pro Ser Gln Arg Pro Thr Phe Lys
            595                 600                 605

Gln Leu Val Glu Asp Leu Asp Arg Val Leu Thr Val Thr Ser Thr Asp
        610                 615                 620

Glu Tyr Leu Asp Leu Ser Ala Pro Phe Glu Gln Tyr Ser Pro Gly Gly
625                 630                 635                 640

Gln Asp Thr Pro Ser Ser Ser Ser Gly Asp Asp Ser Val Phe Ala
                645                 650                 655

His Asp Leu Leu Pro Pro Ala Pro Pro Ser Ser Gly Gly Ser Arg Thr
            660                 665                 670

<210> SEQ ID NO 3
<211> LENGTH: 786
<212> TYPE: PRT
<213> ORGANISM: Homo sapiens

<400> SEQUENCE: 3

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

-continued

```
Met Glu Ser Val Val Pro Ser Asp Arg Gly Asn Tyr Thr Cys Val Val
        195                 200                 205
Glu Asn Lys Phe Gly Ser Ile Arg Gln Thr Tyr Thr Leu Asp Val Leu
        210                 215                 220
Glu Arg Ser Pro His Arg Pro Ile Leu Gln Ala Gly Leu Pro Ala Asn
225                 230                 235                 240
Gln Thr Ala Val Leu Gly Ser Asp Val Glu Phe His Cys Lys Val Tyr
                245                 250                 255
Ser Asp Ala Gln Pro His Ile Gln Trp Leu Lys His Val Glu Val Asn
                260                 265                 270
Gly Ser Lys Val Gly Pro Asp Gly Thr Pro Tyr Val Thr Val Leu Lys
        275                 280                 285
Ser Trp Ile Ser Glu Ser Val Glu Ala Asp Val Arg Leu Arg Leu Ala
        290                 295                 300
Asn Val Ser Glu Arg Asp Gly Gly Glu Tyr Leu Cys Arg Ala Thr Asn
305                 310                 315                 320
Phe Ile Gly Val Ala Glu Lys Ala Phe Trp Leu Ser Val His Gly Pro
                325                 330                 335
Arg Ala Ala Glu Glu Leu Val Glu Ala Asp Glu Ala Gly Ser Val
                340                 345                 350
Tyr Ala Gly Ile Leu Ser Tyr Gly Val Gly Phe Phe Leu Phe Ile Leu
        355                 360                 365
Val Val Ala Ala Val Thr Leu Cys Arg Leu Arg Ser Pro Pro Lys Lys
        370                 375                 380
Gly Leu Gly Ser Pro Thr Val His Lys Ile Ser Arg Phe Pro Leu Lys
385                 390                 395                 400
Arg Gln Val Ser Leu Glu Ser Asn Ala Ser Met Ser Ser Asn Thr Pro
                405                 410                 415
Leu Val Arg Ile Ala Arg Leu Ser Ser Gly Glu Gly Pro Thr Leu Ala
                420                 425                 430
Asn Val Ser Glu Leu Glu Leu Pro Ala Asp Pro Lys Trp Glu Leu Ser
                435                 440                 445
Arg Ala Arg Leu Thr Leu Gly Lys Pro Leu Gly Glu Gly Cys Phe Gly
        450                 455                 460
Gln Val Val Met Ala Glu Ala Ile Gly Ile Asp Lys Asp Arg Ala Ala
465                 470                 475                 480
Lys Pro Val Thr Val Ala Val Lys Met Leu Lys Asp Asp Ala Thr Asp
                485                 490                 495
Lys Asp Leu Ser Asp Leu Val Ser Glu Met Glu Met Lys Met Ile
                500                 505                 510
Gly Lys His Lys Asn Ile Ile Asn Leu Leu Gly Ala Cys Thr Gln Gly
        515                 520                 525
Gly Pro Leu Tyr Val Leu Val Glu Tyr Ala Ala Lys Gly Asn Leu Arg
        530                 535                 540
Glu Phe Leu Arg Ala Arg Arg Pro Pro Gly Leu Asp Tyr Ser Phe Asp
545                 550                 555                 560
Thr Cys Lys Pro Pro Glu Glu Gln Leu Thr Phe Lys Asp Leu Val Ser
                565                 570                 575
Cys Ala Tyr Gln Val Ala Arg Gly Met Glu Tyr Leu Ala Ser Gln Lys
                580                 585                 590
Cys Ile His Arg Asp Leu Ala Ala Arg Asn Val Leu Val Thr Glu Asp
                595                 600                 605
Asn Val Met Lys Ile Ala Asp Phe Gly Leu Ala Arg Asp Val His Asn
```

```
                 610                 615                 620
Leu Asp Tyr Tyr Lys Lys Thr Thr Asn Gly Arg Leu Pro Val Lys Trp
625                 630                 635                 640

Met Ala Pro Glu Ala Leu Phe Asp Arg Val Tyr Thr His Gln Ser Asp
                645                 650                 655

Val Trp Ser Phe Gly Val Leu Leu Trp Glu Ile Phe Thr Leu Gly Gly
                660                 665                 670

Ser Pro Tyr Pro Gly Ile Pro Val Glu Glu Leu Phe Lys Leu Leu Lys
                675                 680                 685

Glu Gly His Arg Met Asp Lys Pro Ala Asn Cys Thr His Asp Leu Tyr
                690                 695                 700

Met Ile Met Arg Glu Cys Trp His Ala Ala Pro Ser Gln Arg Pro Thr
705                 710                 715                 720

Phe Lys Gln Leu Val Glu Asp Leu Asp Arg Val Leu Thr Val Thr Ser
                725                 730                 735

Thr Asp Glu Tyr Leu Asp Leu Ser Ala Pro Phe Glu Gln Tyr Ser Pro
                740                 745                 750

Gly Gly Gln Asp Thr Pro Ser Ser Ser Ser Gly Asp Asp Ser Val
                755                 760                 765

Phe Ala His Asp Leu Leu Pro Pro Ala Pro Pro Ser Ser Gly Gly Ser
770                 775                 780

Arg Thr
785

<210> SEQ ID NO 4
<211> LENGTH: 355
<212> TYPE: PRT
<213> ORGANISM: Homo sapiens

<400> SEQUENCE: 4

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
                35                  40                  45

Pro Thr Val Trp Val Lys Asp Gly Thr Gly Leu Val Pro Ser Glu Arg
50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
                115                 120                 125

Pro Tyr Trp Thr Arg Pro Glu Arg Met Asp Lys Lys Leu Leu Ala Val
                130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
                180                 185                 190

Met Glu Ser Val Val Pro Ser Asp Arg Gly Asn Tyr Thr Cys Val Val
```

```
                195                 200                 205
Glu Asn Lys Phe Gly Ser Ile Arg Gln Thr Tyr Thr Leu Asp Val Leu
210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
            275                 280                 285

Ser Trp Ile Ser Glu Ser Val Glu Ala Asp Val Arg Leu Arg Leu Ala
            290                 295                 300

Asn Val Ser Glu Arg Asp Gly Gly Glu Tyr Leu Cys Arg Ala Thr Asn
305                 310                 315                 320

Phe Ile Gly Val Ala Glu Lys Ala Phe Trp Leu Ser Val His Gly Pro
                325                 330                 335

Arg Ala Ala Glu Glu Glu Leu Val Glu Ala Asp Glu Ala Gly Ser Val
                340                 345                 350

Tyr Ala Gly
        355

<210> SEQ ID NO 5
<211> LENGTH: 353
<212> TYPE: PRT
<213> ORGANISM: Homo sapiens

<400> SEQUENCE: 5

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
                35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
```

```
            210                 215                 220
Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
                275                 280                 285

Thr Ala Gly Ala Asn Thr Thr Asp Lys Glu Leu Glu Val Leu Ser Leu
290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Tyr Ala
                340                 345                 350

Gly

<210> SEQ ID NO 6
<211> LENGTH: 288
<212> TYPE: PRT
<213> ORGANISM: Homo sapiens

<400> SEQUENCE: 6

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
        130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240
```

```
Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
            275                 280                 285

<210> SEQ ID NO 7
<211> LENGTH: 587
<212> TYPE: PRT
<213> ORGANISM: Artificial Sequence
<220> FEATURE:
<223> OTHER INFORMATION: Synthetic polypeptide

<400> SEQUENCE: 7

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
        130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
            275                 280                 285

Ser Trp Ile Ser Glu Ser Val Glu Ala Asp Val Arg Leu Arg Leu Ala
        290                 295                 300

Asn Val Ser Glu Arg Asp Gly Gly Glu Tyr Leu Cys Arg Ala Thr Asn
305                 310                 315                 320
```

```
Phe Ile Gly Val Ala Glu Lys Ala Phe Trp Leu Ser Val His Gly Pro
                325                 330                 335
Arg Ala Ala Glu Glu Leu Val Glu Ala Asp Glu Ala Gly Ser Val
            340                 345                 350
Tyr Ala Gly Glu Pro Lys Ser Ser Asp Lys Thr His Thr Cys Pro Pro
        355                 360                 365
Cys Pro Ala Pro Glu Leu Leu Gly Gly Pro Ser Val Phe Leu Phe Pro
    370                 375                 380
Pro Lys Pro Lys Asp Thr Leu Met Ile Ser Arg Thr Pro Glu Val Thr
385                 390                 395                 400
Cys Val Val Val Asp Val Ser His Glu Asp Pro Glu Val Lys Phe Asn
                405                 410                 415
Trp Tyr Val Asp Gly Val Glu Val His Asn Ala Lys Thr Lys Pro Arg
            420                 425                 430
Glu Glu Gln Tyr Asn Ser Thr Tyr Arg Val Val Ser Val Leu Thr Val
        435                 440                 445
Leu His Gln Asp Trp Leu Asn Gly Lys Glu Tyr Lys Cys Lys Val Ser
    450                 455                 460
Asn Lys Ala Leu Pro Ala Pro Ile Glu Lys Thr Ile Ser Lys Ala Lys
465                 470                 475                 480
Gly Gln Pro Arg Glu Pro Gln Val Tyr Thr Leu Pro Pro Ser Arg Asp
                485                 490                 495
Glu Leu Thr Lys Asn Gln Val Ser Leu Thr Cys Leu Val Lys Gly Phe
            500                 505                 510
Tyr Pro Ser Asp Ile Ala Val Glu Trp Glu Ser Asn Gly Gln Pro Glu
        515                 520                 525
Asn Asn Tyr Lys Thr Thr Pro Pro Val Leu Asp Ser Asp Gly Ser Phe
530                 535                 540
Phe Leu Tyr Ser Lys Leu Thr Val Asp Lys Ser Arg Trp Gln Gln Gly
545                 550                 555                 560
Asn Val Phe Ser Cys Ser Val Met His Glu Ala Leu His Asn His Tyr
                565                 570                 575
Thr Gln Lys Ser Leu Ser Leu Ser Pro Gly Lys
            580                 585

<210> SEQ ID NO 8
<211> LENGTH: 589
<212> TYPE: PRT
<213> ORGANISM: Artificial Sequence
<220> FEATURE:
<223> OTHER INFORMATION: Synthetic polypeptide

<400> SEQUENCE: 8

Glu Ser Leu Gly Thr Glu Gln Arg Val Val Gly Arg Ala Ala Glu Val
1               5                   10                  15
Pro Gly Pro Glu Pro Gly Gln Gln Glu Gln Leu Val Phe Gly Ser Gly
            20                  25                  30
Asp Ala Val Glu Leu Ser Cys Pro Pro Pro Gly Gly Gly Pro Met Gly
        35                  40                  45
Pro Thr Val Trp Val Lys Asp Gly Thr Gly Leu Val Pro Ser Glu Arg
    50                  55                  60
Val Leu Val Gly Pro Gln Arg Leu Gln Val Leu Asn Ala Ser His Glu
65                  70                  75                  80
Asp Ser Gly Ala Tyr Ser Cys Arg Gln Arg Leu Thr Gln Arg Val Leu
                85                  90                  95
Cys His Phe Ser Val Arg Val Thr Asp Ala Pro Ser Ser Gly Asp Asp
```

```
                100                 105                 110
Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
            130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
            275                 280                 285

Ser Trp Ile Ser Glu Ser Val Glu Ala Asp Val Arg Leu Arg Leu Ala
            290                 295                 300

Asn Val Ser Glu Arg Asp Gly Gly Glu Tyr Leu Cys Arg Ala Thr Asn
305                 310                 315                 320

Phe Ile Gly Val Ala Glu Lys Ala Phe Trp Leu Ser Val His Gly Pro
                325                 330                 335

Arg Ala Ala Glu Glu Glu Leu Val Glu Ala Asp Glu Ala Gly Ser Val
            340                 345                 350

Tyr Ala Gly Gly Ser Glu Pro Lys Ser Ser Asp Lys Thr His Thr Cys
            355                 360                 365

Pro Pro Cys Pro Ala Pro Glu Leu Leu Gly Gly Pro Ser Val Phe Leu
370                 375                 380

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
                405                 410                 415

Phe Asn Trp Tyr Val Asp Gly Val Glu Val His Asn Ala Lys Thr Lys
                420                 425                 430

Pro Arg Glu Glu Gln Tyr Asn Ser Thr Tyr Arg Val Val Ser Val Leu
            435                 440                 445

Thr Val Leu His Gln Asp Trp Leu Asn Gly Lys Glu Tyr Lys Cys Lys
            450                 455                 460

Val Ser Asn Lys Ala Leu Pro Ala Pro Ile Glu Lys Thr Ile Ser Lys
465                 470                 475                 480

Ala Lys Gly Gln Pro Arg Glu Pro Gln Val Tyr Thr Leu Pro Pro Ser
                485                 490                 495

Arg Asp Glu Leu Thr Lys Asn Gln Val Ser Leu Thr Cys Leu Val Lys
            500                 505                 510

Gly Phe Tyr Pro Ser Asp Ile Ala Val Glu Trp Glu Ser Asn Gly Gln
            515                 520                 525
```

```
Pro Glu Asn Asn Tyr Lys Thr Thr Pro Pro Val Leu Asp Ser Asp Gly
            530                 535                 540

Ser Phe Phe Leu Tyr Ser Lys Leu Thr Val Asp Lys Ser Arg Trp Gln
545                 550                 555                 560

Gln Gly Asn Val Phe Ser Cys Ser Val Met His Glu Ala Leu His Asn
                565                 570                 575

His Tyr Thr Gln Lys Ser Leu Ser Leu Ser Pro Gly Lys
            580                 585

<210> SEQ ID NO 9
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Gly Pro Met Gly
        35                  40                  45

Pro Thr Val Trp Val Lys Asp Gly Thr Gly Leu Val Pro Ser Glu Arg
50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
290                 295                 300
```

```
His Asn Val Thr Phe Glu Asp Ala Gly Glu Tyr Thr Cys Leu Ala Gly
305                 310                 315                 320

Asn Ser Ile Gly Phe Ser His Ser Ala Trp Leu Val Val Leu Pro
            325                 330                 335

Ala Glu Glu Leu Val Glu Ala Asp Glu Ala Gly Ser Val Tyr Ala
                340                 345                 350

Gly Glu Pro Lys Ser Ser Asp Lys Thr His Thr Cys Pro Pro Cys Pro
                355                 360                 365

Ala Pro Glu Leu Leu Gly Gly Pro Ser Val Phe Leu Phe Pro Pro Lys
370                 375                 380

Pro Lys Asp Thr Leu Met Ile Ser Arg Thr Pro Glu Val Thr Cys Val
385                 390                 395                 400

Val Val Asp Val Ser His Glu Asp Pro Glu Val Lys Phe Asn Trp Tyr
                405                 410                 415

Val Asp Gly Val Glu Val His Asn Ala Lys Thr Lys Pro Arg Glu Glu
                420                 425                 430

Gln Tyr Asn Ser Thr Tyr Arg Val Val Ser Val Leu Thr Val Leu His
                435                 440                 445

Gln Asp Trp Leu Asn Gly Lys Glu Tyr Lys Cys Lys Val Ser Asn Lys
450                 455                 460

Ala Leu Pro Ala Pro Ile Glu Lys Thr Ile Ser Lys Ala Lys Gly Gln
465                 470                 475                 480

Pro Arg Glu Pro Gln Val Tyr Thr Leu Pro Pro Ser Arg Asp Glu Leu
                485                 490                 495

Thr Lys Asn Gln Val Ser Leu Thr Cys Leu Val Lys Gly Phe Tyr Pro
                500                 505                 510

Ser Asp Ile Ala Val Glu Trp Glu Ser Asn Gly Gln Pro Glu Asn Asn
            515                 520                 525

Tyr Lys Thr Thr Pro Pro Val Leu Asp Ser Asp Gly Ser Phe Phe Leu
530                 535                 540

Tyr Ser Lys Leu Thr Val Asp Lys Ser Arg Trp Gln Gln Gly Asn Val
545                 550                 555                 560

Phe Ser Cys Ser Val Met His Glu Ala Leu His Asn His Tyr Thr Gln
                565                 570                 575

Lys Ser Leu Ser Leu Ser Pro Gly Lys
                580                 585

<210> SEQ ID NO 10
<211> LENGTH: 587
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80
```

```
Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
    290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Tyr Ala
            340                 345                 350

Gly Gly Ser Glu Pro Lys Ser Ser Asp Lys Thr His Thr Cys Pro Pro
        355                 360                 365

Cys Pro Ala Pro Glu Leu Leu Gly Gly Pro Ser Val Phe Leu Phe Pro
    370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
        435                 440                 445

Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Asp
                485                 490                 495

Glu Leu Thr Lys Asn Gln Val Ser Leu Thr Cys Leu Val Lys Gly Phe
            500                 505                 510
```

-continued

Tyr Pro Ser Asp Ile Ala Val Glu Trp Glu Ser Asn Gly Gln Pro Glu
            515                 520                 525

Asn Asn Tyr Lys Thr Thr Pro Pro Val Leu Asp Ser Asp Gly Ser Phe
            530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
            565                 570                 575

Thr Gln Lys Ser Leu Ser Leu Ser Pro Gly Lys
            580                 585

<210> SEQ ID NO 11
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
            85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
            130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
            165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
            210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
            245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
            275                 280                 285

```
Thr Ala Gly Ala Asn Thr Thr Asp Lys Glu Leu Glu Val Leu Ser Leu
        290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Leu Val Glu Ala Asp Glu Ala Gly Ser Glu Pro Lys
        340                 345                 350

Ser Ser Asp Lys Thr His Thr Cys Pro Pro Cys Pro Ala Pro Glu Leu
            355                 360                 365

Leu Gly Gly Pro Ser Val Phe Leu Phe Pro Pro Lys Pro Lys Asp Thr
        370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Ala Leu Pro Ala
450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Asp Glu Leu Thr Lys Asn Gln
                485                 490                 495

Val Ser Leu Thr Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
        515                 520                 525

Pro Pro Val Leu Asp Ser Asp Gly Ser Phe Phe Leu Tyr Ser Lys Leu
530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly Lys
                580

<210> SEQ ID NO 12
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
        35                  40                  45

Pro Thr Val Trp Val Lys Asp Gly Thr Gly Leu Val Pro Ser Glu Arg
    50                  55                  60
```

-continued

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
            85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Pro Lys Ser Ser Asp Lys
            340                 345                 350

Thr His Thr Cys Pro Pro Cys Pro Ala Pro Glu Leu Leu Gly Gly Pro
            355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
            435                 440                 445

Tyr Lys Cys Lys Val Ser Asn Lys Ala Leu Pro Ala Pro Ile Glu Lys
450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Thr

-continued

```
                485                 490                 495
Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 13
<211> LENGTH: 576
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Pro Met Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270
```

-continued

```
Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
        290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Gly Pro Lys Ser Ser Asp Lys Thr
            340                 345                 350

His Thr Cys Pro Pro Cys Pro Ala Pro Glu Leu Leu Gly Gly Pro Ser
        355                 360                 365

Val Phe Leu Phe Pro Pro Lys Pro Lys Asp Thr Leu Met Ile Ser Arg
    370                 375                 380

Thr Pro Glu Val Thr Cys Val Val Val Asp Val Ser His Glu Asp Pro
385                 390                 395                 400

Glu Val Lys Phe Asn Trp Tyr Val Asp Gly Val Glu Val His Asn Ala
                405                 410                 415

Lys Thr Lys Pro Arg Glu Glu Gln Tyr Asn Ser Thr Tyr Arg Val Val
            420                 425                 430

Ser Val Leu Thr Val Leu His Gln Asp Trp Leu Asn Gly Lys Glu Tyr
        435                 440                 445

Lys Cys Lys Val Ser Asn Lys Ala Leu Pro Ala Pro Ile Glu Lys Thr
    450                 455                 460

Ile Ser Lys Ala Lys Gly Gln Pro Arg Glu Pro Gln Val Tyr Thr Leu
465                 470                 475                 480

Pro Pro Ser Arg Asp Glu Leu Thr Lys Asn Gln Val Ser Leu Thr Cys
                485                 490                 495

Leu Val Lys Gly Phe Tyr Pro Ser Asp Ile Ala Val Glu Trp Glu Ser
            500                 505                 510

Asn Gly Gln Pro Glu Asn Asn Tyr Lys Thr Thr Pro Pro Val Leu Asp
        515                 520                 525

Ser Asp Gly Ser Phe Phe Leu Tyr Ser Lys Leu Thr Val Asp Lys Ser
    530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly Lys
                565                 570                 575

<210> SEQ ID NO 14
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
        35                  40                  45

Pro Thr Val Trp Val Lys Asp Gly Thr Gly Leu Val Pro Ser Glu Arg
    50                  55                  60
```

-continued

```
Val Leu Val Gly Pro Gln Arg Leu Gln Val Leu Asn Ala Ser His Glu
 65                  70                  75                  80

Asp Ser Gly Ala Tyr Ser Cys Arg Gln Arg Leu Thr Gln Arg Val Leu
                 85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
    290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Pro Lys Ser Ser Asp Lys Thr His Thr Cys Pro
            340                 345                 350

Pro Cys Pro Ala Pro Glu Leu Leu Gly Gly Pro Ser Val Phe Leu Phe
        355                 360                 365

Pro Pro Lys Pro Lys Asp Thr Leu Met Ile Ser Arg Thr Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Asp Glu Leu Thr Lys Asn Gln Val Ser Leu Thr Cys Leu Val Lys Gly
```

```
                    485                 490                 495
Phe Tyr Pro Ser Asp Ile Ala Val Glu Trp Glu Ser Asn Gly Gln Pro
                500                 505                 510

Glu Asn Asn Tyr Lys Thr Thr Pro Pro Val Leu Asp Ser Asp Gly Ser
            515                 520                 525

Phe Phe Leu Tyr Ser Lys Leu Thr Val Asp Lys Ser Arg Trp Gln Gln
        530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 15
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
        35                  40                  45

Pro Thr Val Trp Val Lys Asp Gly Thr Gly Leu Val Pro Ser Glu Arg
50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
```

```
                275                 280                 285
Thr Ala Gly Ala Asn Thr Thr Asp Lys Glu Leu Glu Val Leu Ser Leu
290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Glu Pro Lys
                325                 330                 335

Ser Ser Asp Lys Thr His Thr Cys Pro Pro Cys Pro Ala Pro Glu Leu
            340                 345                 350

Leu Gly Gly Pro Ser Val Phe Leu Phe Pro Pro Lys Pro Lys Asp Thr
        355                 360                 365

Leu Met Ile Ser Arg Thr Pro Glu Val Thr Cys Val Val Val Asp Val
    370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
        435                 440                 445

Pro Ile Glu Lys Thr Ile Ser Lys Ala Lys Gly Gln Pro Arg Glu Pro
    450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
    530                 535                 540

Val Met His Glu Ala Leu His Asn His Tyr Thr Gln Lys Ser Leu Ser
545                 550                 555                 560

Leu Ser Pro Gly Lys
            565

<210> SEQ ID NO 16
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
```

```
                65                  70                  75                  80
Tyr Asn Ser Thr Tyr Arg Val Val Ser Val Leu Thr Val Leu His Gln
                    85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 17
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
```

```
                195                 200                 205
Met His Glu Ala Leu His Asn His Tyr Thr Gln Lys Ser Leu Ser Leu
            210                 215                 220

Ser Pro Gly Lys
225

<210> SEQ ID NO 18
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Trp Ser Trp Lys Cys Leu Leu Phe Trp Ala Val Leu Val Thr Ala
1               5                   10                  15

Thr Leu Cys Thr Ala
            20
```

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Val Ser Trp Gly Arg Phe Ile Cys Leu Val Val Thr Met Ala
1               5                   10                  15

Thr Leu Ser Leu Ala
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Gly Ala Pro Ala Cys Ala Leu Ala Leu Cys Val Ala Val Ala Ile
1               5                   10                  15

Val Ala Gly Ala Ser Ser
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Arg Leu Leu Leu Ala Leu Leu Gly Ile Leu Leu Ser Val Pro Gly
1               5                   10                  15

Pro Pro Val Leu Ser
            20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Ala Pro Ser Ser Gly Asp Asp Glu Asp Gly Glu Asp Glu Ala Glu
1               5                   10                  15

Asp Thr Gly Val Asp Thr Gly
            20

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Asp Glu Asp Gly Glu Asp
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Glu Asp Gly Glu Asp Glu
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Asp Glu Asp Gly Glu Asp Glu Ala Glu
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Asp Glu Asp Gly Glu Asp Glu Ala Glu Asp
1               5                   10

<210> SEQ ID NO 28
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Glu Asp Asp
                100                 105                 110

Asp Asp Asp Asp Glu Ala Glu Asp Thr Gly Val Asp Thr Gly Ala
            115                 120                 125

```
Pro Tyr Trp Thr Arg Pro Glu Arg Met Asp Lys Lys Leu Leu Ala Val
    130                 135                 140
Pro Ala Ala Asn Thr Val Arg Phe Arg Cys Pro Ala Ala Gly Asn Pro
145                 150                 155                 160
Thr Pro Ser Ile Ser Trp Leu Lys Asn Gly Arg Glu Phe Arg Gly Glu
            165                 170                 175
His Arg Ile Gly Gly Ile Lys Leu Arg His Gln Gln Trp Ser Leu Val
        180                 185                 190
Met Glu Ser Val Val Pro Ser Asp Arg Gly Asn Tyr Thr Cys Val Val
    195                 200                 205
Glu Asn Lys Phe Gly Ser Ile Arg Gln Thr Tyr Thr Leu Asp Val Leu
210                 215                 220
Glu Arg Ser Pro His Arg Pro Ile Leu Gln Ala Gly Leu Pro Ala Asn
225                 230                 235                 240
Gln Thr Ala Val Leu Gly Ser Asp Val Glu Phe His Cys Lys Val Tyr
            245                 250                 255
Ser Asp Ala Gln Pro His Ile Gln Trp Leu Lys His Val Glu Val Asn
        260                 265                 270
Gly Ser Lys Val Gly Pro Asp Gly Thr Pro Tyr Val Thr Val Leu Lys
    275                 280                 285
Thr Ala Gly Ala Asn Thr Thr Asp Lys Glu Leu Glu Val Leu Ser Leu
290                 295                 300
His Asn Val Thr Phe Glu Asp Ala Gly Glu Tyr Thr Cys Leu Ala Gly
305                 310                 315                 320
Asn Ser Ile Gly Phe Ser His His Ser Ala Trp Leu Val Val Leu Pro
            325                 330                 335
Ala Glu Glu Glu Leu Val Glu Ala Asp Glu Ala Gly Ser Val Tyr Ala
        340                 345                 350
Gly Glu Pro Lys Ser Ser Asp Lys Thr His Thr Cys Pro Pro Cys Pro
    355                 360                 365
Ala Pro Glu Leu Leu Gly Gly Pro Ser Val Phe Leu Phe Pro Pro Lys
370                 375                 380
Pro Lys Asp Thr Leu Met Ile Ser Arg Thr Pro Glu Val Thr Cys Val
385                 390                 395                 400
Val Val Asp Val Ser His Glu Asp Pro Glu Val Lys Phe Asn Trp Tyr
            405                 410                 415
Val Asp Gly Val Glu Val His Asn Ala Lys Thr Lys Pro Arg Glu Glu
        420                 425                 430
Gln Tyr Asn Ser Thr Tyr Arg Val Val Ser Val Leu Thr Val Leu His
    435                 440                 445
Gln Asp Trp Leu Asn Gly Lys Glu Tyr Lys Cys Lys Val Ser Asn Lys
450                 455                 460
Ala Leu Pro Ala Pro Ile Glu Lys Thr Ile Ser Lys Ala Lys Gly Gln
465                 470                 475                 480
Pro Arg Glu Pro Gln Val Tyr Thr Leu Pro Pro Ser Arg Asp Glu Leu
            485                 490                 495
Thr Lys Asn Gln Val Ser Leu Thr Cys Leu Val Lys Gly Phe Tyr Pro
        500                 505                 510
Ser Asp Ile Ala Val Glu Trp Glu Ser Asn Gly Gln Pro Glu Asn Asn
    515                 520                 525
Tyr Lys Thr Thr Pro Pro Val Leu Asp Ser Asp Gly Ser Phe Phe Leu
530                 535                 540
Tyr Ser Lys Leu Thr Val Asp Lys Ser Arg Trp Gln Gln Gly Asn Val
545                 550                 555                 560
```

```
Phe Ser Cys Ser Val Met His Glu Ala Leu His Asn His Tyr Thr Gln
            565                 570                 575

Lys Ser Leu Ser Leu Ser Pro Gly Lys
            580                 585

<210> SEQ ID NO 29
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335
```

```
Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly
    370                 375

<210> SEQ ID NO 30
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Ser Leu Gly Thr Glu Gln Arg Val Val Gly Arg Ala Ala Glu Val
1               5                   10                  15

Pro Gly Pro Glu Pro Gly Gln Glu Gln Leu Val Phe Gly Ser Gly
            20                  25                  30

Asp Ala Val Glu Leu Ser Cys Pro Pro Gly Gly Pro Met Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65              70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
    290                 295                 300

His Asn Val Thr Phe Glu Asp Ala Gly Glu Tyr Thr Cys Leu Ala Gly
305                 310                 315                 320
```

Asn Ser Ile Gly Phe Ser His His Ser Ala Trp Leu Val Val Leu Pro
              325                 330                 335

Ala Glu Glu Glu Leu Val Glu Ala Asp Glu Ala Gly Ser Val
              340                 345                 350

<210> SEQ ID NO 31
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
              20                  25                  30

Arg Leu Cys Cys Gly Arg Ala Glu Arg Gly Gly His Trp Tyr Lys Glu
              35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
              85                  90                  95

Gly Asp Ala Leu Pro Ser Ser Glu Asp Asp Asp Asp Asp Asp Asp Ser
              100                 105                 110

Ser Ser Glu Glu Lys Glu Thr Asp Asn Thr Lys Pro Asn Pro Val Ala
              115                 120                 125

Pro Tyr Trp Thr His Pro Gln Arg Met Glu Lys Lys Leu His Ala Val
              130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
              165                 170                 175

Asn Arg Ile Gly Gly Ile Arg Leu Arg His Gln His Trp Ser Leu Val
              180                 185                 190

Met Glu Ser Val Val Pro Ser Asp Arg Gly Thr Tyr Thr Cys Leu Val
              195                 200                 205

Glu Asn Ala Val Gly Ser Ile Arg Tyr Asn Tyr Leu Leu Asp Val Leu
              210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
              245                 250                 255

Ser Asp Ala Gln Pro His Ile Gln Trp Leu Lys His Ile Val Ile Asn
              260                 265                 270

Gly Ser Ser Phe Gly Ala Asp Gly Phe Pro Tyr Val Gln Val Leu Lys
              275                 280                 285

Thr Ala Asp Ile Asn Ser Ser Glu Val Glu Val Leu Tyr Leu Arg Asn
              290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro Glu Pro
              325                 330                 335

```
Lys Ser Ser Asp Lys Thr His Thr Cys Pro Pro Cys Pro Ala Pro Glu
                340                 345                 350

Leu Leu Gly Gly Pro Ser Val Phe Leu Phe Pro Pro Lys Pro Lys Asp
            355                 360                 365

Thr Leu Met Ile Ser Arg Thr Pro Glu Val Thr Cys Val Val Val Asp
        370                 375                 380

Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
                405                 410                 415

Ser Thr Tyr Arg Val Val Ser Val Leu Thr Val Leu His Gln Asp Trp
            420                 425                 430

Leu Asn Gly Lys Glu Tyr Lys Cys Lys Val Ser Asn Lys Ala Leu Pro
        435                 440                 445

Ala Pro Ile Glu Lys Thr Ile Ser Lys Ala Lys Gly Gln Pro Arg Glu
450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
        515                 520                 525

Leu Thr Val Asp Lys Ser Arg Trp Gln Gln Gly Asn Val Phe Ser Cys
530                 535                 540

Ser Val Met His Glu Ala Leu His Asn His Tyr Thr Gln Lys Ser Leu
545                 550                 555                 560

Ser Leu Ser Pro Gly Lys
                565

<210> SEQ ID NO 32
<211> LENGTH: 587
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125
```

```
Asn Lys Arg Ala Pro Tyr Trp Thr Asn Thr Glu Lys Met Glu Lys Arg
    130                 135                 140

Leu His Ala Val Pro Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
            340                 345                 350

Asp Gly Ser Glu Pro Lys Ser Ser Asp Lys Thr His Thr Cys Pro Pro
        355                 360                 365

Cys Pro Ala Pro Glu Leu Leu Gly Gly Pro Ser Val Phe Leu Phe Pro
    370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
        435                 440                 445

Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Asp
                485                 490                 495

Glu Leu Thr Lys Asn Gln Val Ser Leu Thr Cys Leu Val Lys Gly Phe
            500                 505                 510

Tyr Pro Ser Asp Ile Ala Val Glu Trp Glu Ser Asn Gly Gln Pro Glu
        515                 520                 525

Asn Asn Tyr Lys Thr Thr Pro Pro Val Leu Asp Ser Asp Gly Ser Phe
    530                 535                 540

Phe Leu Tyr Ser Lys Leu Thr Val Asp Lys Ser Arg Trp Gln Gln Gly
```

```
                545                 550                 555                 560
Asn Val Phe Ser Cys Ser Val Met His Glu Ala Leu His Asn His Tyr
                565                 570                 575
Thr Gln Lys Ser Leu Ser Leu Ser Pro Gly Lys
                580                 585

<210> SEQ ID NO 33
<211> LENGTH: 584
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ser Leu Gly Thr Glu Gln Arg Val Val Gly Arg Ala Ala Glu Val
1               5                   10                  15
Pro Gly Pro Glu Pro Gly Gln Gln Glu Gln Leu Val Phe Gly Ser Gly
                20                  25                  30
Asp Ala Val Glu Leu Ser Cys Pro Pro Pro Gly Gly Gly Pro Met Gly
            35                  40                  45
Pro Thr Val Trp Val Lys Asp Gly Thr Gly Leu Val Pro Ser Glu Arg
        50                  55                  60
Val Leu Val Gly Pro Gln Arg Leu Gln Val Leu Asn Ala Ser His Glu
65                  70                  75                  80
Asp Ser Gly Ala Tyr Ser Cys Arg Gln Arg Leu Thr Gln Arg Val Leu
                85                  90                  95
Cys His Phe Ser Val Arg Val Thr Asp Ala Pro Ser Ser Gly Asp Asp
                100                 105                 110
Glu Asp Gly Glu Asp Glu Ala Glu Asp Thr Gly Val Asp Thr Gly Ala
            115                 120                 125
Pro Tyr Trp Thr Arg Pro Glu Arg Met Asp Lys Lys Leu Leu Ala Val
        130                 135                 140
Pro Ala Ala Asn Thr Val Arg Phe Arg Cys Pro Ala Ala Gly Asn Pro
145                 150                 155                 160
Thr Pro Ser Ile Ser Trp Leu Lys Asn Gly Arg Glu Phe Arg Gly Glu
                165                 170                 175
His Arg Ile Gly Gly Ile Lys Leu Arg His Gln Gln Trp Ser Leu Val
                180                 185                 190
Met Glu Ser Val Val Pro Ser Asp Arg Gly Asn Tyr Thr Cys Val Val
            195                 200                 205
Glu Asn Lys Phe Gly Ser Ile Arg Gln Thr Tyr Thr Leu Asp Val Leu
        210                 215                 220
Glu Arg Ser Pro His Arg Pro Ile Leu Gln Ala Gly Leu Pro Ala Asn
225                 230                 235                 240
Gln Thr Ala Val Leu Gly Ser Asp Val Glu Phe His Cys Lys Val Tyr
                245                 250                 255
Ser Asp Ala Gln Pro His Ile Gln Trp Leu Lys His Val Glu Val Asn
                260                 265                 270
Gly Ser Lys Val Gly Pro Asp Gly Thr Pro Tyr Val Thr Val Leu Lys
            275                 280                 285
Thr Ala Gly Ala Asn Thr Thr Asp Lys Glu Leu Glu Val Leu Ser Leu
        290                 295                 300
His Asn Val Thr Phe Glu Asp Ala Gly Glu Tyr Thr Cys Leu Ala Gly
305                 310                 315                 320
Asn Ser Ile Gly Phe Ser His His Ser Ala Trp Leu Val Val Leu Pro
```

```
                    325                 330                 335
Ala Glu Glu Glu Leu Val Glu Ala Asp Glu Ala Gly Ser Val Gly Ser
            340                 345                 350

Glu Pro Lys Ser Ser Asp Lys Thr His Thr Cys Pro Pro Cys Pro Ala
            355                 360                 365

Pro Glu Leu Leu Gly Gly Pro Ser Val Phe Leu Phe Pro Pro Lys Pro
            370                 375                 380

Lys Asp Thr Leu Met Ile Ser Arg Thr Pro Glu Val Thr Cys Val Val
385                 390                 395                 400

Val Asp Val Ser His Glu Asp Pro Glu Val Lys Phe Asn Trp Tyr Val
            405                 410                 415

Asp Gly Val Glu Val His Asn Ala Lys Thr Lys Pro Arg Glu Glu Gln
            420                 425                 430

Tyr Asn Ser Thr Tyr Arg Val Val Ser Val Leu Thr Val Leu His Gln
            435                 440                 445

Asp Trp Leu Asn Gly Lys Glu Tyr Lys Cys Lys Val Ser Asn Lys Ala
            450                 455                 460

Leu Pro Ala Pro Ile Glu Lys Thr Ile Ser Lys Ala Lys Gly Gln Pro
465                 470                 475                 480

Arg Glu Pro Gln Val Tyr Thr Leu Pro Pro Ser Arg Asp Glu Leu Thr
            485                 490                 495

Lys Asn Gln Val Ser Leu Thr Cys Leu Val Lys Gly Phe Tyr Pro Ser
            500                 505                 510

Asp Ile Ala Val Glu Trp Glu Ser Asn Gly Gln Pro Glu Asn Asn Tyr
            515                 520                 525

Lys Thr Thr Pro Pro Val Leu Asp Ser Asp Gly Ser Phe Phe Leu Tyr
            530                 535                 540

Ser Lys Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
            565                 570                 575

Ser Leu Ser Leu Ser Pro Gly Lys
            580

<210> SEQ ID NO 34
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
            50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
            85                  90                  95

Cys His Phe Ser Val Arg Val Thr Asp Ala Pro Ser Ser Glu Asp Asp
```

```
                100                 105                 110
Asp Asp Asp Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
            130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
            210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
            290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Tyr Ala
            340                 345                 350

Gly

<210> SEQ ID NO 35
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Glu Asp Asp
                100                 105                 110
```

```
Asp Asp Asp Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
        130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
        210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
        290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Glu Pro
            340                 345                 350

Lys Ser Ser Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
        370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Ala Leu Pro
        450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Asp Glu Leu Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
        515                 520                 525

Thr Pro Pro Val Leu Asp Ser Asp Gly Ser Phe Phe Leu Tyr Ser Lys
```

```
                      530                 535                 540
Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                    565                 570                 575

Ser Leu Ser Pro Gly Lys
            580

<210> SEQ ID NO 36
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Glu Asp Asp
                100                 105                 110

Asp Asp Asp Asp Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
        130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
                180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
        210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
        290                 295                 300

His Asn Val Thr Phe Glu Asp Ala Gly Glu Tyr Thr Cys Leu Ala Gly
```

Asn Ser Ile Gly Phe Ser His His Ser Ala Trp Leu Val Val Leu Pro
            325                 330                 335

Ala Glu Glu Glu Leu Val Glu Ala Asp Glu Ala Gly Ser Val
            340                 345                 350

<210> SEQ ID NO 37
<211> LENGTH: 584
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Glu Asp Asp
            100                 105                 110

Asp Asp Asp Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
        130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
        290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro

```
                        325                 330                 335
Ala Glu Glu Glu Leu Val Glu Ala Asp Glu Ala Gly Ser Val Gly Ser
                340                 345                 350

Glu Pro Lys Ser Ser Asp Lys Thr His Thr Cys Pro Pro Cys Pro Ala
            355                 360                 365

Pro Glu Leu Leu Gly Gly Pro Ser Val Phe Leu Phe Pro Pro Lys Pro
        370                 375                 380

Lys Asp Thr Leu Met Ile Ser Arg Thr Pro Glu Val Thr Cys Val Val
385                 390                 395                 400

Val Asp Val Ser His Glu Asp Pro Glu Val Lys Phe Asn Trp Tyr Val
                405                 410                 415

Asp Gly Val Glu Val His Asn Ala Lys Thr Lys Pro Arg Glu Glu Gln
            420                 425                 430

Tyr Asn Ser Thr Tyr Arg Val Val Ser Val Leu Thr Val Leu His Gln
        435                 440                 445

Asp Trp Leu Asn Gly Lys Glu Tyr Lys Cys Lys Val Ser Asn Lys Ala
    450                 455                 460

Leu Pro Ala Pro Ile Glu Lys Thr Ile Ser Lys Ala Lys Gly Gln Pro
465                 470                 475                 480

Arg Glu Pro Gln Val Tyr Thr Leu Pro Pro Ser Arg Asp Glu Leu Thr
                485                 490                 495

Lys Asn Gln Val Ser Leu Thr Cys Leu Val Lys Gly Phe Tyr Pro Ser
            500                 505                 510

Asp Ile Ala Val Glu Trp Glu Ser Asn Gly Gln Pro Glu Asn Asn Tyr
        515                 520                 525

Lys Thr Thr Pro Pro Val Leu Asp Ser Asp Gly Ser Phe Phe Leu Tyr
    530                 535                 540

Ser Lys Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Pro Gly Lys
            580

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Ser Leu Thr Ser Ser Asn Asp Asp Glu Asp Pro Lys Ser His Arg
1               5                   10                  15

Asp Pro Ser Asn Arg His Ser Tyr Pro Gln Gln
            20                  25

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ala Leu Pro Ser Ser Glu Asp Asp Asp Asp Asp Asp Ser Ser
1               5                   10                  15
```

```
Ser Glu Glu Lys Glu Thr Asp Asn Thr Lys Pro Asn Pro Val
            20                  25                  30

<210> SEQ ID NO 40
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Ala Ile Ser Ser Gly Asp Asp Glu Asp Thr Asp Gly Ala Glu
1               5                   10                  15

Asp Phe Val Ser Glu Asn Ser Asn Asn Lys Arg
            20                  25

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Asp Glu Asp Gly Glu
1               5

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Asp Asp Glu Asp Gly Glu Asp Glu Ala Glu Asp
1               5                   10

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Asp Glu Asp
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Tyr Ala Gly
1

<210> SEQ ID NO 45
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Ala Gly Ser Val Tyr Ala Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Glu Ala Gly Ser Val Tyr Ala Gly
1               5

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Val Glu Ala Asp Glu Ala Gly Ser Val Tyr Ala Gly
1               5                   10

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Leu Pro Ala Glu Glu Glu Leu Val Glu Ala Asp Glu Ala Gly Ser
1               5                   10                  15

Val Tyr Ala Gly
            20

<210> SEQ ID NO 49
<211> LENGTH: 23
<212> TYPE: PRT
<213> ORGANISM: Homo sapiens

<400> SEQUENCE: 49

Leu Lys His Val Glu Val Asn Gly Ser Lys Val Gly Pro Asp Gly Thr
1               5                   10                  15

Pro Tyr Val Thr Val Leu Lys
            20

<210> SEQ ID NO 50
<211> LENGTH: 90
<212> TYPE: PRT
<213> ORGANISM: Homo sapiens

<400> SEQUENCE: 50

Leu Lys His Val Glu Val Asn Gly Ser Lys Val Gly Pro Asp Gly Thr
1               5                   10                  15
```

```
Pro Tyr Val Thr Val Leu Lys Ser Trp Ile Ser Glu Ser Val Glu Ala
            20                  25                  30

Asp Val Arg Leu Arg Leu Ala Asn Val Ser Glu Arg Asp Gly Gly Glu
        35                  40                  45

Tyr Leu Cys Arg Ala Thr Asn Phe Ile Gly Val Ala Glu Lys Ala Phe
    50                  55                  60

Trp Leu Ser Val His Gly Pro Arg Ala Ala Glu Glu Glu Leu Val Glu
65                  70                  75                  80

Ala Asp Glu Ala Gly Ser Val Tyr Ala Gly
                85                  90

<210> SEQ ID NO 51
<211> LENGTH: 88
<212> TYPE: PRT
<213> ORGANISM: Homo sapiens

<400> SEQUENCE: 51

Leu Lys His Val Glu Val Asn Gly Ser Lys Val Gly Pro Asp Gly Thr
1               5                   10                  15

Pro Tyr Val Thr Val Leu Lys Thr Ala Gly Ala Asn Thr Thr Asp Lys
            20                  25                  30

Glu Leu Glu Val Leu Ser Leu His Asn Val Thr Phe Glu Asp Ala Gly
        35                  40                  45

Glu Tyr Thr Cys Leu Ala Gly Asn Ser Ile Gly Phe Ser His His Ser
    50                  55                  60

Ala Trp Leu Val Val Leu Pro Ala Glu Glu Leu Val Glu Ala Asp
65                  70                  75                  80

Glu Ala Gly Ser Val Tyr Ala Gly
                85

<210> SEQ ID NO 52
<211> LENGTH: 89
<212> TYPE: PRT
<213> ORGANISM: Homo sapiens

<400> SEQUENCE: 52

Leu Lys His Ile Glu Val Asn Gly Ser Lys Ile Gly Pro Asp Asn Leu
1               5                   10                  15

Pro Tyr Val Gln Ile Leu Lys His Ser Gly Ile Asn Ser Ser Asp Ala
            20                  25                  30

Glu Val Leu Thr Leu Phe Asn Val Thr Glu Ala Gln Ser Gly Glu Tyr
        35                  40                  45

Val Cys Lys Val Ser Asn Tyr Ile Gly Glu Ala Asn Gln Ser Ala Trp
    50                  55                  60

Leu Thr Val Thr Arg Pro Val Ala Lys Ala Leu Glu Glu Arg Pro Ala
65                  70                  75                  80

Val Met Thr Ser Pro Leu Tyr Leu Glu
                85

<210> SEQ ID NO 53
<211> LENGTH: 87
<212> TYPE: PRT
<213> ORGANISM: Homo sapiens

<400> SEQUENCE: 53

Leu Lys His Ile Glu Val Asn Gly Ser Lys Ile Gly Pro Asp Asn Leu
1               5                   10                  15

Pro Tyr Val Gln Ile Leu Lys Thr Ala Gly Val Asn Thr Thr Asp Lys
```

-continued

```
                 20                  25                  30

Glu Met Glu Val Leu His Leu Arg Asn Val Ser Phe Glu Asp Ala Gly
             35                  40                  45

Glu Tyr Thr Cys Leu Ala Gly Asn Ser Ile Gly Leu Ser His His Ser
         50                  55                  60

Ala Trp Leu Thr Val Leu Glu Ala Leu Glu Glu Arg Pro Ala Val Met
 65                  70                  75                  80

Thr Ser Pro Leu Tyr Leu Glu
                 85

<210> SEQ ID NO 54
<211> LENGTH: 88
<212> TYPE: PRT
<213> ORGANISM: Homo sapiens

<400> SEQUENCE: 54

Ile Lys His Val Glu Lys Asn Gly Ser Lys Tyr Gly Pro Asp Gly Leu
 1               5                  10                  15

Pro Tyr Leu Lys Val Leu Lys His Ser Gly Ile Asn Ser Ser Asn Ala
             20                  25                  30

Glu Val Leu Ala Leu Phe Asn Val Thr Glu Ala Asp Ala Gly Glu Tyr
         35                  40                  45

Ile Cys Lys Val Ser Asn Tyr Ile Gly Gln Ala Asn Gln Ser Ala Trp
     50                  55                  60

Leu Thr Val Leu Pro Lys Gln Gln Ala Pro Gly Arg Glu Lys Glu Ile
 65                  70                  75                  80

Thr Ala Ser Pro Asp Tyr Leu Glu
                 85

<210> SEQ ID NO 55
<211> LENGTH: 87
<212> TYPE: PRT
<213> ORGANISM: Homo sapiens

<400> SEQUENCE: 55

Ile Lys His Val Glu Lys Asn Gly Ser Lys Tyr Gly Pro Asp Gly Leu
 1               5                  10                  15

Pro Tyr Leu Lys Val Leu Lys Ala Ala Gly Val Asn Thr Thr Asp Lys
             20                  25                  30

Glu Ile Glu Val Leu Tyr Ile Arg Asn Val Thr Phe Glu Asp Ala Gly
         35                  40                  45

Glu Tyr Thr Cys Leu Ala Gly Asn Ser Ile Gly Ile Ser Phe His Ser
     50                  55                  60

Ala Trp Leu Thr Val Leu Pro Ala Pro Gly Arg Glu Lys Glu Ile Thr
 65                  70                  75                  80

Ala Ser Pro Asp Tyr Leu Glu
                 85

<210> SEQ ID NO 56
<211> LENGTH: 86
<212> TYPE: PRT
<213> ORGANISM: Homo sapiens

<400> SEQUENCE: 56

Leu Lys His Ile Val Ile Asn Gly Ser Ser Phe Gly Ala Asp Gly Phe
 1               5                  10                  15

Pro Tyr Val Gln Val Leu Lys Thr Ala Asp Ile Asn Ser Ser Glu Val
             20                  25                  30
```

-continued

```
Glu Val Leu Tyr Leu Arg Asn Val Ser Ala Glu Asp Ala Gly Glu Tyr
            35                  40                  45

Thr Cys Leu Ala Gly Asn Ser Ile Gly Leu Ser Tyr Gln Ser Ala Trp
 50                  55                  60

Leu Thr Val Leu Pro Glu Glu Asp Pro Thr Trp Thr Ala Ala Ala Pro
 65                  70                  75                  80

Glu Ala Arg Tyr Thr Asp
                85

<210> SEQ ID NO 57
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SIGNAL
<222> LOCATION: (1)..(22)
<220> FEATURE:
<221> NAME/KEY: mat_peptide
<222> LOCATION: (23)..(372)

<400> SEQUENCE: 57

Met Gly Ala Pro Ala Cys Ala Leu Ala Leu Cys Val Ala Val Ala Ile
                -20                 -15                 -10

Val Ala Gly Ala Ser Ser Glu Ser Leu Gly Thr Glu Gln Arg Val Val
     -5                  -1   1                   5                  10

Gly Arg Ala Ala Glu Val Pro Gly Pro Glu Pro Gly Gln Gln Glu Gln
                 15                  20                  25

Leu Val Phe Gly Ser Gly Asp Ala Val Glu Leu Ser Cys Pro Pro Pro
                 30                  35                  40

Gly Gly Gly Pro Met Gly Pro Thr Val Trp Val Lys Asp Gly Thr Gly
                 45                  50                  55

Leu Val Pro Ser Glu Arg Val Leu Val Gly Pro Gln Arg Leu Gln Val
                 60                  65                  70

Leu Asn Ala Ser His Glu Asp Ser Gly Ala Tyr Ser Cys Arg Gln Arg
 75                  80                  85                  90

Leu Thr Gln Arg Val Leu Cys His Phe Ser Val Arg Val Thr Asp Ala
                 95                 100                 105

Pro Ser Ser Gly Asp Asp Glu Asp Gly Glu Asp Glu Ala Glu Asp Thr
                110                 115                 120

Gly Val Asp Thr Gly Ala Pro Tyr Trp Thr Arg Pro Gly Arg Met Asp
                125                 130                 135

Lys Lys Leu Leu Ala Val Pro Ala Ala Asn Thr Val Arg Phe Arg Cys
140                 145                 150

Pro Ala Ala Gly Asn Pro Thr Pro Ser Ile Ser Trp Leu Lys Asn Gly
155                 160                 165                 170

Arg Glu Phe Arg Gly Glu His Arg Ile Gly Gly Ile Lys Leu Arg His
                175                 180                 185

Gln Gln Trp Ser Leu Val Met Glu Ser Val Val Pro Ser Asp Arg Gly
                190                 195                 200

Asn Tyr Thr Cys Val Val Glu Asn Lys Phe Gly Ser Ile Arg Gln Thr
                205                 210                 215

Tyr Thr Leu Asp Val Leu Glu Arg Ser Pro His Arg Pro Ile Leu Gln
                220                 225                 230

Ala Gly Leu Pro Ala Asn Gln Thr Ala Val Leu Gly Ser Asp Val Glu
235                 240                 245                 250
```

-continued

```
Phe His Cys Lys Val Tyr Ser Asp Ala Gln Pro His Ile Gln Trp Leu
            255                 260                 265

Lys His Val Glu Val Asn Gly Ser Lys Val Gly Pro Asp Gly Thr Pro
            270                 275                 280

Tyr Val Thr Val Leu Lys Thr Ala Gly Ala Asn Thr Thr Asp Lys Glu
        285                 290                 295

Leu Glu Val Leu Ser Leu His Asn Val Thr Phe Glu Asp Ala Gly Glu
        300                 305                 310

Tyr Thr Cys Leu Ala Gly Asn Ser Ile Gly Phe Ser His His Ser Ala
315                 320                 325                 330

Trp Leu Val Val Leu Pro Ala Glu Glu Glu Leu Val Glu Ala Asp Glu
            335                 340                 345

Ala Gly Ser Val
            350
```

HAIR GROWTH METHODS USING FGFR3 EXTRACELLULAR DOMAINS

This application claims priority to U.S. Provisional Application No. 61/287,690, filed Dec. 17, 2009, which is incorporated by reference herein.

TECHNICAL FIELD

The present invention relates to a method of promoting hair growth comprising administering an FGFR3 extracellular domain (ECD), including native FGFR3 ECDs, variants, fragments, and fusion molecules, to a subject in an amount sufficient to promote hair growth.

BACKGROUND AND SUMMARY

Hair growth problems are wide-spread. In addition to pattern baldness, which may occur in both males and females, hair loss can be induced by drugs, such as chemotherapy drugs, or by chemical or physical damage, such as by certain hair products or styling techniques. Hair loss may also be triggered by systemic diseases, autoimmune conditions, nutritional deficiencies and physical stress, such as during pregnancy, due to surgery, or due to weight loss. It may also be induced by psychological stress.

Available treatments to promote hair growth are limited. For example, minoxidil, while relatively safe, is only moderately effective. The 5-alpha reductase inhibitor finasteride is not indicated for women or children and has negative side effects. The use of certain polypeptides to promote hair growth has been suggested. (See e.g., U.S. Pat. No. 7,335,641, U.S. Pat. No. 7,524,505, U.S. Pat. No. 7,485,618, and U.S. Patent Application No. 2008/0139469.) To date, the only permanent solution to hair loss is hair transplant surgery, which is both expensive and invasive. Thus, there remains a need in the art for additional agents for promoting hair growth. The present disclosure relates to a method of promoting hair growth comprising administering a fibroblast growth factor receptor 3 (FGFR3) extracellular domain (ECD) to a subject in an amount sufficient to promote hair growth.

Fibroblast growth factors (FGFs) and their receptors (FGFRs) are a highly conserved group of proteins with diverse functions. The FGFR family comprises four major types of receptors, FGFR1, FGFR2, FGFR3, and FGFR4. To date, there are 22 known FGFs, each with the capacity to bind one or more FGFRs. See, e.g., Zhang et al, *J. Biol. Chem.* 281:15, 694-15,700 (2006). Each FGFR binds to several FGFs, and the different FGFRs may differ from each other both in the selection of FGFs to which they bind as well as in the affinity of those interactions.

The FGFRs are transmembrane proteins having an extracellular domain (ECD), a transmembrane domain, and an intracytoplasmic tyrosine kinase domain. Extracellular FGFR activation by FGF ligand binding to an FGFR initiates a cascade of signaling events inside the cell, beginning with oligomerization of the receptor and activation of receptor tyrosine kinase activity. Each of the ECDs contains either two or three immunoglobulin-like (Ig) domains. When there are three Ig domains, they are referred to as D1, D2, and D3 domains. Receptors having two Ig domains typically lack D1. An acidic motif, called the acid box, is located in the linker region between D1 and D2 in the FGFR extracellular domain. The acid box is believed to interact with the heparin binding site in the D2 domain. Structural studies of FGFR-FGF complexes have shown that FGF ligands interact extensively with the D2 domain, the D3 domain, and the linker region connecting the D2 and D3 domains of an FGFR ECD. In FGFR1-3, an alternative splicing event leads to three versions of the D3 domain, also called Ig domain III. The splice variants of this domain are referred to as domain Δ8-10, IIIb and IIIc. Domain III or D3 is encoded by three exons, two of which are alternatively spliced. Distinct splice variants of FGFR3 have been identified in a range of tissues and cancers, such as FGFR3 IIIb, FGFR3 IIIc, and FGFR Δ8-10 (lacking exons encoding the C-terminal half of Ig domain III and the transmembrane domain). See, e.g., Tomlinson et al., *Cancer Res.* 65: 10,441-10,449 (2005).

In experiments to determine whether an FGFR4 ECD exhibited antitumor activity in a cancer xenograft model, the inventors discovered that an FGFR4 ECD promoted hair growth at the shaved site where the tumor cells were injected. In contrast, an FGFR1 ECD did not promote visible hair growth. In subsequent experiments, both a native FGFR4 ECD fragment fusion molecule and an FGFR4 ECD variant fusion molecule ("ABMut1") that retained FGFR4 ECD ligand binding activity promoted hair growth when administered systemically in mice. Experiments in which ABMut1 or agarose beads bound to ABMut1 were subcutaneously injected into the flank of shaved mice showed that local delivery of ABMut1 also promoted hair growth. Further experiments demonstrated that systemic delivery of ABMut1 could also induce anagen in hair follicles, specifically elongation of the dermal papilla into the fatty layer of the dermis. The inventors conducted similar studies with a native FGFR3 ECD fragment fusion molecule and discovered that the FGFR3 ECD fragment promoted hair growth when administered systemically in mice. In contrast, an FGFR2 ECD did not promote visible hair growth. Further experiments demonstrated that the FGFR3 ECD fragment fusion molecule could also induce anagen in hair follicles, specifically elongation of the dermal papilla into the fatty layer of the dermis, while the FGFR2 ECD did not have that effect. See Example 6, FIG. 3A and FIG. 3B. Yet further experiments demonstrate that the FGFR3 ECD fragment fusion molecule stimulates hair growth in a dose dependent manner. See Example 7, FIG. 4.

In certain embodiments, the invention provides a method of promoting hair growth comprising administering an FGFR3 ECD to a subject in an amount sufficient to promote hair growth. In certain embodiments, the FGFR3 ECD is a human FGFR3 ECD. In certain embodiments, the FGFR3 ECD is a non-human FGFR3 ECD. In certain embodiments, the FGFR3 ECD is a native FGFR3 ECD. In certain embodiments, the FGFR3 ECD is an FGFR3 ECD variant. In certain embodiments, the FGFR3 ECD is an FGFR3 ECD splice variant. In certain embodiments, the FGFR3 ECD comprises an Ig domain III chosen from Δ8-10, IIIb and IIIc (the FGFR3 ECD is also referred to as FGFR3-Δ8-10 ECD, FGFR3-IIIb ECD, or FGFR3-IIIc ECD). In certain embodiments, the FGFR3 ECD is an FGFR3 ECD fragment. In certain embodiments, the FGFR3 ECD is a native FGFR3 ECD fragment. In certain embodiments, the FGFR3 ECD is a variant of an FGFR3 ECD fragment. In certain embodiments, the FGFR3 ECD is a fragment of an FGFR3 ECD splice variant. In certain embodiments, the FGFR3 ECD is an FGFR3 LCD acidic region mutein. In certain embodiments, the FGFR3 ECD may be engineered to have a decrease in the total number of acidic residues within the D1-D2 linker. In certain embodiments, the FGFR3 ECD is an FGFR3 ECD D1-D2 linker chimera. In certain embodiments, the FGFR3 ECD D1-D2 linker chimera comprises a D1-D2 linker selected from an FGFR1 D1-D2 linker, an FGFR2 D1-D2 linker, and an FGFR4 D1-D2 linker, in place of the FGFR3 D1-D2 linker.

In certain embodiments, the FGFR3 ECD is an FGFR3 ECD glycosylation mutant. In certain embodiments, the amino acid sequence of the FGFR3 ECD is at least 80% identical to SEQ ID NO: 4, 5, 6, or 30. In certain embodiments, the amino acid sequence of the FGFR3 ECD is at least 85% identical to SEQ ID NO: 4, 5, 6, or 30. In certain embodiments, the amino acid sequence of the FGFR3 ECD is at least 90% identical to SEQ ID NO: 4, 5, 6, or 30. In certain embodiments, the amino acid sequence of the FGFR3 ECD is at least 95% identical to SEQ ID NO: 4, 5, 6, or 30. In certain embodiments, the amino acid sequence of the FGFR3 ECD is at least 99% identical to SEQ ID NO: 4, 5, 6, or 30. In certain embodiments, the FGFR3 ECD comprises an amino acid sequence chosen from SEQ ID NOs: 4, 5, 6, or 30. In certain embodiments, the FGFR3 ECD comprises an amino acid sequence chosen from SEQ ID NOs: 34 and 36. In certain embodiments, the FGFR3 ECD lacks a signal sequence. In certain embodiments, the FGFR3 ECD comprises a signal sequence. In certain embodiments, the signal sequence is the native signal sequence of FGFR1, FGFR2, FGFR3, or FGFR4 (SEQ ID NOs: 19-22). In certain embodiments, the signal sequence is not an FGFR signal sequence, but from a heterologous protein.

In certain embodiments, the subject is a rodent, simian, human, feline, canine, equine, bovine, porcine, ovine, caprine, mammalian laboratory animal, mammalian farm animal, mammalian sport animal, or mammalian pet. In certain embodiments, the subject is a human. In certain embodiments, the administering is intravenous, subcutaneous, intraperitoneal, topical, or transdermal.

In certain embodiments, the invention provides a method of growing hair comprising administering an FGFR3 ECD fusion molecule to a subject in an amount sufficient to promote hair growth. In certain embodiments, the FGFR3 ECD fusion molecule comprises an FGFR3 ECD polypeptide and a fusion partner. In certain embodiments, the FGFR3 ECD polypeptide is a native FGFR3 ECD. In certain embodiments, the FGFR3 ECD polypeptide is an FGFR3 ECD variant. In certain embodiments, the FGFR3 ECD polypeptide is an FGFR3 ECD splice variant. In certain embodiments, the FGFR3 ECD polypeptide is FGFR3-Δ8-10 ECD, FGFR3-IIIb ECD, or FGFR3-IIIc ECD. In certain embodiments, the FGFR3 ECD polypeptide is an FGFR3 ECD fragment. In certain embodiments, the FGFR3 ECD polypeptide is a native FGFR3 ECD fragment. In certain embodiments, the FGFR3 ECD polypeptide is a variant of an FGFR3 ECD fragment. In certain embodiments, the FGFR3 ECD polypeptide is a fragment of an FGFR3 ECD splice variant. In certain embodiments, the FGFR3 ECD polypeptide is an FGFR3 ECD acidic region mutein. In certain embodiments, the FGFR3 ECD polypeptide may be engineered to have a decrease in the total number of acidic residues within the D1-D2 linker. In certain embodiments, the FGFR3 ECD polypeptide is an FGFR3 ECD D1-D2 linker chimera. In certain embodiments, the FGFR3 ECD D1-D2 linker chimera comprises a D1-D2 linker selected from an FGFR1 D1-D2 linker, an FGFR2 D1-D2 linker, and an FGFR4 D1-D2 linker, in place of the FGFR3 D1-D2 linker. In certain embodiments, the FGFR3 ECD polypeptide is an FGFR3 ECD glycosylation mutant. In certain embodiments, the amino acid sequence of the FGFR3 ECD polypeptide is at least 80% identical to SEQ ID NO: 4, 5, 6, or 30. In certain embodiments, the amino acid sequence of the FGFR3 ECD polypeptide is at least 85% identical to SEQ ID NO: 4, 5, 6, or 30. In certain embodiments, the amino acid sequence of the FGFR3 ECD polypeptide is at least 90% identical to SEQ ID NO: 4, 5, 6, or 30. In certain embodiments, the amino acid sequence of the FGFR3 ECD polypeptide is at least 95% identical to SEQ ID NO: 4, 5, 6, or 30. In certain embodiments, the amino acid sequence of the FGFR3 ECD polypeptide is at least 99% identical to SEQ ID NO: 4, 5, 6, or 30. In certain embodiments, the FGFR3 ECD polypeptide comprises an amino acid sequence chosen from SEQ ID NOs: 4, 5, 6, and 30. In certain embodiments, the FGFR3 ECD polypeptide comprises an amino acid sequence chosen from SEQ ID NOs: 34 and 36. In certain embodiments, the FGFR3 ECD polypeptide lacks a signal sequence. In certain embodiments, the FGFR3 ECD comprises a signal sequence. In certain embodiments, the signal sequence is the native signal sequence of FGFR1, FGFR2, FGFR3, or FGFR4 (SEQ ID NOs: 19-22). In certain embodiments, the signal sequence is not an FGFR signal sequence, but from a heterologous protein.

In certain embodiments, a method of growing hair comprising administering an FGFR3 ECD fusion molecule to a subject in an amount sufficient to promote hair growth is provided, wherein the fusion partner in the FGFR3 ECD fusion molecule is selected from an Fc, albumin, and polyethylene glycol. In certain embodiments, the fusion partner is an Fc. In certain embodiments, the FGFR3 ECD fusion molecule has an amino acid sequence chosen from SEQ ID NOs: 7-10. In certain embodiments, the FGFR3 ECD fusion molecule has an amino acid sequence chosen from SEQ ID NOs: 11-15, 28, 31-33, 35 and 37. In certain embodiments, the FGFR3 ECD fusion molecule has an amino acid sequence chosen from SEQ ID NO.: 9, 10 and 33. In certain embodiments, the FGFR3 ECD fusion molecule lacks a signal sequence. In certain embodiments, the FGFR3 ECD fusion molecule comprises a signal sequence. In certain embodiments, the signal sequence is the native signal sequence of FGFR1, FGFR2, FGFR3, or FGFR4. In certain embodiments, the signal sequence is not an FGFR signal sequence.

BRIEF DESCRIPTION OF THE DRAWINGS

FIG. 2 shows an amino acid sequence alignment of a portion of the native extracellular domains (ECDs) of the FGFR isoforms FGFR3-Δ8-10 (SEQ ID NO: 49), FGFR3-IIIb (SEQ ID NO: 50), FGFR3-IIIc (SEQ ID NO: 51), FGFR1-IIIb (SEQ ID NO: 52), FGFR1-IIIc (SEQ ID NO: 53), FGFR2-IIIb (SEQ ID NO: 54), FGFR2-IIIc (SEQ ID NO: 55), and FGFR4 (SEQ ID NO: 56), denoting the immunoglobulin (Ig) domain III.

FIG. 3A shows that systemic delivery of an FGFR3 ECD-Fc (SEQ ID NO: 33) and ABMut1 (SEQ ID NO: 31, an FGFR4 ECD variant-Fc), promotes a substantial amount of clearly visible hair growth by 14 days post-dose, compared to vehicle-treated mice and mice treated with an FGFR2 ECD-Fc (SEQ ID NO: 32) by 14 days post-dose.

FIG. 4 shows that an FGFR3 ECD-Fc stimulates hair growth in mice in a dose dependent manner.

DETAILED DESCRIPTION OF CERTAIN EMBODIMENTS

Figure 1:
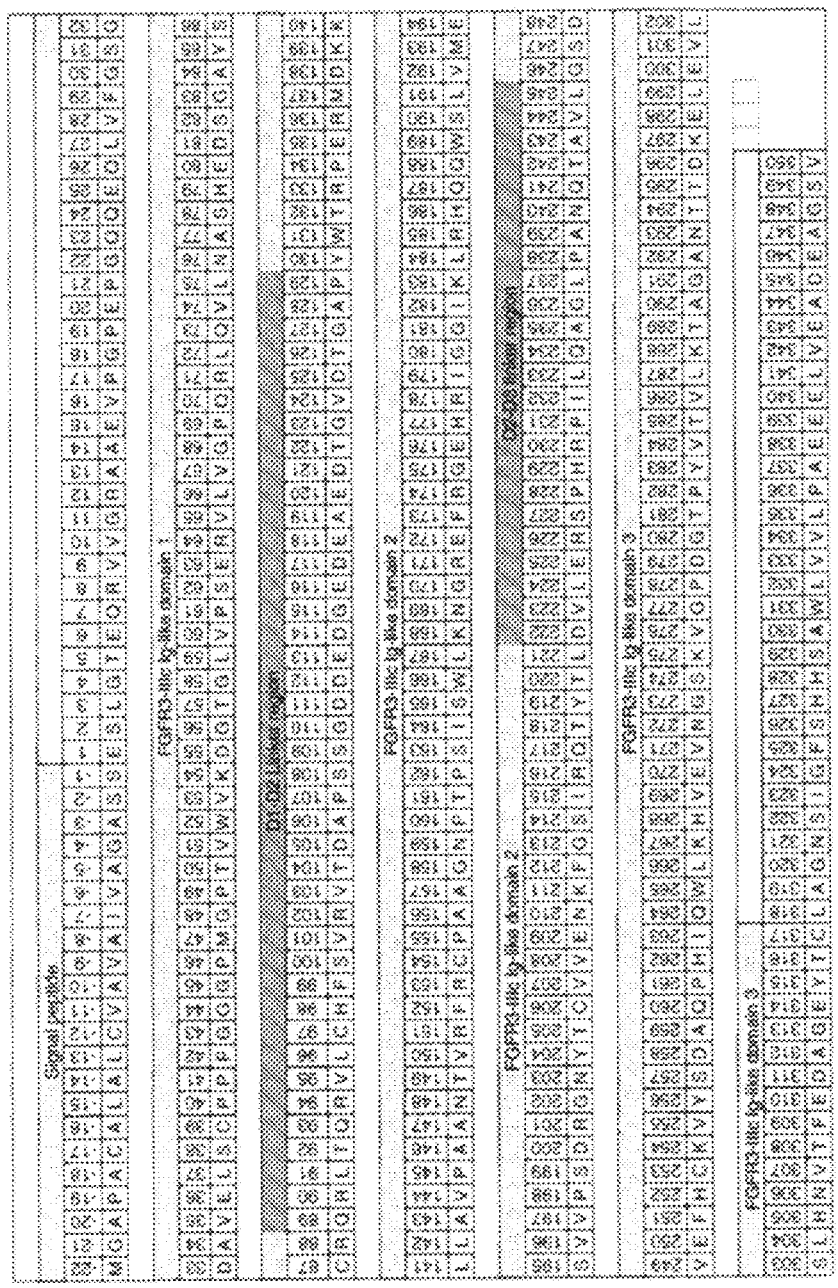
FIG. 1 shows an extracellular domain (ECD) amino acid sequence of an FGFR3 (SEQ ID NO: 29). The amino acid sequence in FIG. 1 includes the signal peptide, which is cleaved in the mature fusion protein. The numbers refer to the amino acid position, and certain domains within the ECD are illustrated in gray above the amino acid numbers. The amino acid positions within the signal peptide are given negative values because they are cleaved in the mature fusion protein. The first amino acid residue of the mature fusion protein is designated as amino acid position 1. The signal peptide and domains D1, D2, and D3 are noted in gray shading. The linker between the first and second Ig domains (referred to herein interchangeably as the "D1-D2 linker," "FGFR3 ECD D1-D2 linker" and "FGFR3 ECD D1-D2 linker region") and the linker between the second and third Ig domains (referred to herein interchangeably as the "D2-D3 linker," "FGFR3 ECD D2-D3 linker," and "FGFR3 ECD D2-D3 linker region") are illustrated in a darker gray.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2d ed., Cold Spring Harbor Laboratory Press, Cold Spring Harbor, N.Y. (1989)), among other places. In addition, certain techniques for chemical syntheses, chemical analyses, pharmaceutical preparation, formulation, delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA.

The terms "polypeptide" and "protein" are used interchangeably, and refer to a polymer of amino acid residues. Such polymers of amino acid residues may contain natural and/or non-natural amino acid residues, and include, but are not limited to, peptides, oligopeptides, dimers, trimers, and multimers of amino acid residues. The terms "polypeptide" and "protein" include natural and non-natural amino acid sequences, and both full-length proteins and fragments thereof. Those terms also include post-translationally modified polypeptides and proteins, including, for example, glycosylated, sialylated, acetylated, and/or phosphorylated polypeptides and proteins.

The terms "acidic amino acid," "acidic amino acid residue," and "acidic residue" are used interchangeably herein and refer to an amino acid residue that is negatively charged at physiological pH. Acidic amino acids include, but are not limited to, aspartic acid (Asp, D) and glutamic acid (Glu, E).

The terms "non-acidic amino acid," "non-acidic amino acid residue," and "non-acidic residue" are used interchangeably and refer to an amino acid residue that is not negatively charged at physiological pH.

The terms "conservative amino acid substitutions" and "conservative substitutions" are used interchangeably herein to refer to intended amino acid swaps within a group of amino acids wherein an amino acid is exchanged with a different amino acid of similar size, structure, charge, and/or polarity. Examples include exchange of one of the aliphatic or hydrophobic amino acids Ala, Val, Leu, and Ile for one of the other amino acids in that group of four; exchange between the hydroxyl-containing residues Ser and Thr; exchange between the acidic residues Asp and Glu; exchange between the amide residues Asn and Gln, exchange between the basic residues Lys, Arg, and His; exchange between the aromatic residues Phe, Tyr, and Trp; and exchange between the small-sized amino acids Ala, Ser, Thr, Met, and Gly.

The terms "FGFR extracellular domain" and "FGFR ECD" in the context of this invention refer to the portion of an FGFR that is normally found in the extracellular space. An FGFR ECD may include the amino-terminal residues that precede the D1 domain, the D1 domain, the D1-D2 linker region, the D2 domain, the D2-D3 linker region, the D3 domain (Ig domain III), and the carboxy-terminal residues that follow the D3 domain.

The terms "FGFR3 extracellular domain" and "FGFR3 ECD" as used herein refer to a genus consisting of the following sub-genuses: native FGFR3 ECDs, FGFR3 ECD variants, FGFR3 ECD fragments, native FGFR3 ECD fragments, variants of FGFR3 ECD fragments, FGFR3 ECD acidic region muteins, FGFR3 ECDs engineered to have a decrease in the total number of acidic residues within the D1-D2 linker, FGFR3 ECD D1-D2 linker chimeras, FGFR3 ECD glycosylation mutants, and FGFR3 ECD fusion molecules, as well as non-human FGFR3 ECDs. FGFR3 ECDs can include those annotated as NP_001156685, P22607, NP_000133, or NP_075254, as described by the National Center of Bioinformatics Information (NCBI). The FGFR3 ECDs as defined herein bind FGF1 and/or FGF18 as tested herein. See Example 5.

As used herein, the terms "native FGFR3 ECD" and "wild-type FGFR3 ECD" are used interchangeably to refer to an FGFR3 ECD consisting of an amino acid sequence selected from SEQ ID NOs: 4, 5, and 6. Native FGFR3 ECDs and wild-type FGFR3 ECDs include FGFR3 ECD splice variants or isoforms. As used herein, the terms FGFR3 ECD "splice variants" or "splice isoforms" are used interchangeably to refer to naturally occurring alternative splice forms of FGFR3 ECD, such as FGFR3-Δ8-10 ECD (SEQ ID NO: 6), FGFR3-IIIb (ECD SEQ ID NO: 4) and FGFR3-IIIc ECD (SEQ ID NO: 5), which comprise an Ig domain III chosen from Δ8-10, IIIb, and IIIc, respectively.

As used herein, the term "FGFR3-Δ8-10 ECD" refers to the FGFR3 ECD with an Ig domain III chosen from native FGFR3 Δ8-10 (see SEQ ID NO: 6) and Δ8-10 variants. The term "FGFR3-IIIb ECD" refers to the FGFR3 ECD with an Ig domain III chosen from native IIIb (see SEQ ID NO: 4) and IIIb variants. The term "FGFR3-IIIc ECD" refers to the FGFR3 ECD with an Ig domain III chosen from native IIIc (see SEQ ID NO: 5) and IIIc variants.

As used herein, the term "FGFR3 ECD variants" refers to FGFR3 ECDs containing amino acid additions, deletions, and/or substitutions in comparison to the native FGFR3 ECDs, such as those of SEQ ID NOs: 4, 5, and 6. Amino acid additions and deletions may be made at the amino-terminus, at the carboxy-terminus, and/or within SEQ ID NOs: 4, 5, and 6. An exemplary FGFR3 ECD variant that contains amino acid deletions has the amino acid sequence of SEQ ID No: 30. FGFR3 ECD variants may include amino acid substitutions within the FGFR3 ECD that inhibit N-glycosylation, referred to interchangeably herein as "FGFR3 ECD glycosylation mutants" and "FGFR3 ECD N-glycan mutants." The FGFR3 ECD variants as defined herein retain the ability to bind FGF1 and/or FGF18 as tested herein.

As used herein, the term "native FGFR3 ECD fragment" refers to an FGFR3 ECD having an amino acid sequence selected from SEQ ID NOs: 4, 5, and 6, but modified in that amino acid residues have been deleted from the amino-terminus and/or from the carboxy-terminus of the polypeptide. A non-limiting exemplary FGFR3 ECD fragment has the amino acid sequence of SEQ ID NO: 30, which corresponds to the amino acid sequence of SEQ ID NO: 5, but with the last three carboxy-terminal amino acid residues, YAG, deleted.

As used herein, the terms "FGFR3 ECD fragment variant" and "variant of FGFR3 ECD fragment" are used interchangeably to refer to FGFR3 ECDs containing, not only amino acid deletions from the amino- and/or carboxy-terminus of SEQ ID NOs: 4, 5, and 6, but also amino acid additions, deletions, and/or substitutions within the retained portion of SEQ ID NOs: 4, 5, and 6.

Collectively, "native FGFR3 ECD fragments" and "FGFR3 ECD fragment variants" form the genus of "FGFR3 ECD fragments." FGFR3 ECD fragments as defined herein retain the ability to bind FGF1 and/or FGF18 as tested herein.

The term "FGFR3 ECD D1 domain" refers to the first Ig domain of a native FGFR3 ECD. The native FGFR3 ECD D1 domain consists of the sequence of amino acids 31-88, inclusive, of SEQ ID NO: 4, SEQ ID NO: 5, or SEQ ID NO: 6. (See also FIG. 1.)

The term "FGFR3 ECD D2 domain" refers to the second Ig domain of a native FGFR3 ECD. The native FGFR3 ECD D2 domain consists of the sequence of amino acids 129-221, inclusive, of SEQ ID NO: 4, SEQ ID NO: 5, or SEQ ID NO: 6. (See also FIG. 1.)

The term "FGFR3 ECD D3 domain" refers to the third Ig domain (Ig domain III) of a native FGFR3 ECD. The native FGFR3 ECD D3 domain consists of the sequence of amino acids 246-317, inclusive, of SEQ ID NO: 5; or consists of the sequence of amino acids 231-327, inclusive, of SEQ ID NO: 4. (See also FIG. 1.)

The terms "FGFR3 ECD D1-D2 linker" and "FGFR3 ECD D1-D2 linker region" are used interchangeably to refer to the linker between the first and second Ig domains (the D1 and D2 domains, respectively) of the FGFR3 ECD. The FGFR3 ECD D1-D2 linker has the sequence DAPSSGDDEDGEDE-AEDTGVDTG (SEQ ID NO: 23), which is amino acids 105 to 127, inclusive, of SEQ ID NO: 4, SEQ ID NO: 5, or SEQ ID NO: 6. (See also FIG. 1.)

The terms "FGFR3 ECD D2-D3 linker" and "FGFR3 ECD D2-D3 linker region" are used interchangeably to refer to the linker between the second and third Ig domains (the D2 and D3 domains, respectively) of the FGFR3 ECD. (See also FIG. 1.)

As used herein, an "FGFR3 ECD acidic region mutein" is an FGFR3 ECD variant having a greater or smaller number of acidic residues in the D1-D2 linker region than the native FGFR3 ECD D1-D2 linker region. An exemplary FGFR3 ECD acidic region has the amino acid sequence chosen from SEQ ID NOs: 24-27 and 41-43.

An "FGFR3 ECD D1-D2 linker chimera" refers to an FGFR3 ECD acidic region mutein wherein the D1-D2 linker region has been replaced with the D1-D2 linker region from FGFR1, FGFR2, or FGFR4. In certain exemplary D1-D2 linker chimeras, the D1-D2 linker of the FGFR3 ECD is exchanged for a D1-D2 linker of FGFR 1: DALPSSED-DDDDDDSSSEEKETDNTKPNPV (SEQ ID NO: 39). In certain exemplary D1-D2 linker chimeras, the D1-D2 linker of the FGFR3 ECD is exchanged for a D1-D2 linker of FGFR2: DAISSGDDED DTDGAEDFVS ENSNNKR (SEQ ID NO: 40). In certain exemplary D1-D2 linker chimeras, the D1-D2 linker of the FGFR3 ECD is exchanged for a D1-D2 linker of FGFR4: DSLTSSNDDED PKSHRDPSNR HSYPQQ (SEQ II) NO: 38). The FGFR3 ECD linker chimeras as defined herein retain the ability to bind FGF1 and/or FGF18 as tested herein.

FGFR3 ECD variants may include amino acid substitutions within the FGFR3 ECD sequence that inhibit N-glycosylation, referred to interchangeably herein as "FGFR3 ECD glycosylation mutants" and "FGFR3 ECD N-glycan mutants." In certain embodiments, one or more amino acids are mutated to prevent glycosylation at that site in the polypeptide. Non-limiting exemplary FGFR3 ECD amino acids that may be glycosylated include N76, N203, N240, N272, N293, and N306 in SEQ ID NO: 5. Accordingly, one or more of those amino acids may be substituted. Non-limiting exemplary amino acid mutations in FGFR3 ECD glycosylation mutants include N76A, N203A, N240A, N272A, N293A, and N306A in SEQ ID NO: 5. The FGFR3 ECD glycosylation mutants as defined herein retain the ability to bind FGF1 and/or FGF18 as tested herein.

The terms "FGFR3 ECD fusion molecule" and "FGFR3 ECD fusion" are used interchangeably herein to refer to an FGFR3 ECD comprising an FGFR3 ECD polypeptide and a fusion partner. FGFR3 ECD fusions may be constructed based upon any of the FGFR3 ECD genera defined above or any of the FGFR3 ECD species described elsewhere herein. The fusion partner may be linked to either the amino-terminus or the carboxy-terminus of the polypeptide. In certain embodiments, the polypeptide and the fusion partner are covalently linked. If the fusion partner is also a polypeptide ("the fusion partner polypeptide"), the polypeptide and the fusion partner polypeptide may be part of a continuous amino acid sequence. In such cases, the polypeptide and the fusion partner polypeptide may be translated as a single polypeptide from a coding sequence that encodes both the polypeptide and the fusion partner polypeptide. In certain embodiments, the polypeptide and the fusion partner are covalently linked through other means, such as, for example, a chemical linkage other than a peptide bond. Many methods of covalently linking polypeptides to other molecules (for example, fusion partners) are known in the art. The FGFR3 ECD fusion molecules as defined herein retain the ability to bind FGF1 and/or FGF18 as tested herein.

In certain embodiments, the polypeptide and the fusion partner are noncovalently linked. In certain such embodiments, they may be linked, for example, using binding pairs. Exemplary binding pairs include, but are not limited to, biotin and avidin or streptavidin, an antibody and its antigen, etc.

Certain exemplary fusion partners include, but are not limited to, an immunoglobulin Fc domain, albumin, and polyethylene glycol. The amino acid sequences of certain exemplary Fc domains are shown in SEQ ID NOs: 16-18. Exemplary FGFR3 ECD Fc fusions include those shown in Table 4 below.

In certain embodiments, the FGFR3 amino acid sequence is derived from that of a non-human mammal. Such FGFR3 are termed "non-human FGFR3." In such embodiments, the FGFR3 sequence may be derived from mammals including, but not limited to, rodents, simians, felines, canines, equines, bovines, porcines, ovines, caprines, mammalian laboratory animals, mammalian farm animals, mammalian sport animals, and mammalian pets. Known non-human FGFR3 sequences include those with GenBank Accession Nos. NP_001156687, NP_001156688, NP_001156689, NP_445881, NP_990840, and NP_776743. Such FGFR3 sequences can be modified in the same way as the human FGFR3 sequences described above. In other words, non-human FGFR3 includes the corresponding native FGFR3, FGFR3 variants, FGFR3 fragments, native FGFR3 fragments, variants of FGFR3 fragments, and FGFR3 fusion molecules.

In certain embodiments, the FGFR3 ECD amino acid sequence is derived from that of a non-human mammal. Such FGFR3 ECDs are termed "non-human FGFR3 ECDs." In such embodiments, the FGFR3 ECD sequence may be derived from mammals including, but not limited to, rodents, simians, felines, canines, equines, bovines, porcines, ovines, caprines, mammalian laboratory animals, mammalian farm animals, mammalian sport animals, and mammalian pets. Known non-human FGFR3 ECD sequences include those annaoted as such in sequences identified by GenBank Accession Nos. NP_001156687, NP_001156688, NP_001156689, NP_445881, NP_990840, and NP_776743. Such FGFR3 ECD sequences can be modified in the same way as the human FGFR3 ECD sequences described above. In other words, non-human FGFR3 ECDs include the corresponding native FGFR3 ECDs, FGFR3 ECD variants, FGFR3 ECD fragments, native FGFR3 ECD fragments, variants of FGFR3 ECD fragments, FGFR3-Δ8-10 ECDs, FGFR3-IIIb ECDs, and FGFR3-IIIc ECDs, FGFR3 ECD acidic region muteins, FGFR3 ECD D1-D2 linker chimeras, FGFR3 ECD glycosylation mutants, and FGFR3 ECD fusion molecules. The non-human FGFR3 ECD as defined herein are able to bind the corresponding non-human FGF1 and/or FGF18 as tested herein.

The terms "signal peptide" and "signal sequence" are used interchangeably herein to refer to a sequence of amino acid residues that facilitates secretion of a polypeptide from a mammalian cell. A signal peptide is typically cleaved upon export of the polypeptide from the mammalian cell. Certain exemplary signal peptides include, but are not limited to, the native signal peptides of FGFR1, FGFR2, FGFR3, and FGFR4, such as, for example, the amino acid sequences of SEQ ID NOs: 19-22. Certain exemplary signal peptides also include signal peptides from heterologous proteins. Other exemplary signal peptides also include signal peptides from non-human proteins such as non-human FGFR1, FGFR2, FGFR3, and FGFR4. A "signal sequence" refers to a polynucleotide sequence that encodes a signal peptide.

A "vector" refers to a polynucleotide that is used to express a polypeptide of interest in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, e.g., β-galactosidase).

A "host cell" refers to a cell that can be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Certain exemplary mammalian cells include, but are not limited to, 293 and CHO cells.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "subject" is used herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

"Treatment," as used herein, covers any administration or application of a therapeutic for disease in a mammal, including a human, and includes inhibiting the disease or progression of the disease, partially inhibiting or slowing the disease or its progression, arresting its development, partially or fully relieving the disease, or curing the disease, for example, by causing regression, or restoring or repairing a lost, missing, or defective function; or stimulating an inefficient process.

"Administration," as used herein, includes both self-administration by the subject as well as administration by another individual, such as a physician, nurse, or veterinarian.

A "pharmaceutically acceptable carrier" refers to a non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the composition is to be administered orally, the carrier may be a gel capsule. If the composition is to be administered subcutaneously, the carrier ideally is not irritable to the skin and does not cause injection site reaction.

FGFR3 ECDs

As defined above, an FGFR3 ECD is a genus consisting of the following sub-genuses: native FGFR3 ECDs, FGFR3 ECD variants, FGFR3 ECD fragments, native FGFR3 ECD fragments, variants of FGFR3 ECD fragments, FGFR3 ECD acidic region muteins, FGFR3 ECDs engineered to have a decrease in the total number of acidic residues within the D1-D2 linker, FGFR3 ECD D1-D2 linker chimeras, FGFR3 ECD glycosylation mutants, and FGFR3 ECD fusion molecules, as well as non-human FGFR3 ECDs. FGFR3 ECDs can include those annotated as NP_001156685, P22607, NP_000133, or NP_075254, as described by the National Center of Bioinformatics Information (NCBI). The FGFR3 ECDs as defined herein bind FGF1 and/or FGF18 as tested herein. (See Example 5).

Description of the method used herein to test FGF1 and FGF18 binding by FGFR3 ECD is provided in Example 5. A Biacore® T100 surface plasmon resonance (SPR) technology-based assay was used to measure binding of FGF ligands to FGFR3 ECD. In certain embodiments, an FGFR3 ECD binds to FGF1 with an equilibrium dissociation constant ($K_D$) value no more than 100 nM, or with a $K_D$ value no more than 10 nM, or with a $K_D$ value no more than 1 nM, or with a $K_D$ value no more than 0.1 nM, in a Biacore® T100 ligand binding assay. (See Example 5.) In certain embodiments, an FGFR3 ECD binds to FGF18 with a $K_D$ value no more than 100 nM, or with a $K_D$ value no more than 10 nM, or with a $K_D$ value no more than 1 nM, with a $K_D$ value no more than 0.1 nM, or with a $K_D$ value no more than 0.01 nM, in a Biacore® T100 ligand binding assay. (Id.)

Signal Peptides

Typically, the signal peptide is cleaved from the mature FGFR3 ECD polypeptide. Thus, in many embodiments, the FGFR3 ECD lacks a signal peptide. Nonetheless, in certain embodiments, an FGFR3 ECD includes at least one signal peptide, which may be selected from a native FGFR3 signal peptide and/or a heterologous signal peptide. In some embodiments, the FGFR3 ECD comprises a signal sequence at its amino terminus. Any one of the above genuses of polypeptides defined above or the polypeptide species described herein may further include a signal peptide. Exemplary signal peptides include, but are not limited to, the signal peptides of FGFR1, FGFR2, FGFR3, and FGFR4, such as, for example, the amino acid sequences of SEQ ID NOs: 19 to 22. In other embodiments, the signal peptide may be a signal peptide from a heterologous protein.

FGFR3 ECD Fusion Molecules and Their Construction

In some embodiments, the FGFR3 ECD is a fusion molecule. Accordingly, any one of the genuses of polypeptides defined above or the polypeptide species described herein may further include a fusion partner. FGFR3 ECD fusion molecules comprising an FGFR3 ECD polypeptide and a fusion partner may be used in the methods herein.

Certain exemplary FGFR3 ECD fusion molecules are provided in Table 4. For example, an exemplary FGFR3-IIIb ECD Fc fusion (SEQ ID NO: 7) is a native FGFR3-IIIb ECD fused to an Fc. An exemplary FGFR3-IIIb ECD Fc fusion with a GS linker has the amino acid sequence of SEQ ID NO: 8. An exemplary FGFR3-IIIc ECD Fc fusion (SEQ ID NO: 9) is a native FGFR3-IIIc ECD fused to an Fc. An exemplary FGFR3-IIIc ECD Fc fusion with a GS linker has the amino acid sequence of SEQ ID NO: 10. FGFR3-IIIc ECD Δ3Fc fusion with a GS linker (SEQ ID NO: 33) is a native FGFR3-IIIc ECD fragment with a 3 amino acid C-terminal deletion fused to an Fc through the linker glycine-serine ("GS"). Certain exemplary FGFR3 ECD fusion molecules also are shown in SEQ ID NO: 11 (a native FGFR3-IIIc ECD fragment with a 4 amino acid C-terminal deletion fused to an Fc), SEQ ID NO: 12 (a native FGFR3-IIIc ECD fragment with a 8 amino acid C-terminal deletion fused to an Fc), SEQ ID NO: 13 (a native FGFR3-IIIc ECD fragment with a 9 amino acid C-terminal deletion fused to an Fc), SEQ ID NO: 14 (a native FGFR3-IIIc ECD fragment with a 13 amino acid C-terminal deletion fused to an Fc), SEQ ID NO: 15 (a native FGFR3-IIIc ECD fragment with a 20 amino acid C-terminal deletion fused to an Fc), SEQ ID NO: 28, SEQ ID NO: 35, and SEQ ID NO: 37.

Fusion Partners and Conjugates

In certain embodiments, a fusion partner is selected that imparts favorable pharmacokinetics and/or pharmacodynamics on the FGFR3 ECD fusion molecule.

Non-limiting exemplary fusion partners include polymers, polypeptides, lipophilic moieties, and succinyl groups. Exemplary polypeptide fusion partners include serum albumin and an antibody Fc domain. Exemplary polymer fusion partners include, but are not limited to, polyethylene glycol (PEG), including polyethylene glycols having branched and/or linear chains. Some embodiments may include more than one fusion partner, such as an Fc and a polymer fusion partner such as PEG.

Oligomerization Domain Fusion Partners

In various embodiments, oligomerization offers certain functional advantages to a fusion protein, including, but not limited to, multivalency, increased binding strength, and the combined function of different domains. Accordingly, in certain embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains, and certain immunoglobulin domains. Certain exemplary coiled-coil polypeptide fusion partners include the tetranectin coiled-coil domain; the coiled-coil domain of cartilage oligomeric matrix protein; angiopoietin coiled-coil domains; and leucine zipper domains. Certain exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that could be used as fusion partners are known in the art. In certain embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Certain additional Fc fusion partners include, but are not limited to, those from human IgA and IgM. In certain embodiments, an Fc fusion partner is that from a human IgG1 In certain embodiments, an Fc fusion partner is from a human IgG1 and comprises a C237S mutation. In certain embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs: 16-18.

Certain exemplary FGFR3 ECD fusion molecules comprise, but are not limited to, polypeptides having the amino acid sequences of SEQ ID NOs: 7-15, 28, 35 and 37.

Albumin Fusion Partners and Albumin-Binding Molecule Fusion Partners

In certain embodiments, a fusion partner is an albumin. Certain exemplary albumins include, but are not limited to, human serum album (HSA) and fragments of HSA that are capable of increasing the serum half-life and/or bioavailability of the polypeptide to which they are fused. In certain embodiments, a fusion partner is an albumin-binding molecule, such as, for example, a peptide that binds albumin or a molecule that conjugates with a lipid or other molecule that binds albumin. In certain embodiments, a fusion molecule comprising HSA is prepared as described, e.g., in U.S. Pat. No. 6,686,179.

Polymer Fusion Partners

In certain embodiments, a fusion partner is a polymer, for example, polyethylene glycol (PEG). PEG may comprise branched and/or linear chains. In certain embodiments, a fusion partner comprises a chemically-derivatized polypeptide having at least one PEG moiety attached. Pegylation of a polypeptide may be carried out by any method known in the art. Certain exemplary PEG attachment methods include, for example, EP 0 401 384; Malik et al., *Exp. Hematol.*, 20:1028-1035 (1992); Francis, *Focus an Growth Factors*, 3:4-10 (1992); EP 0 154 316; EP 0 401 384; WO 92/16221; and WO 95/34326. As non-limiting examples, pegylation may be performed via an acylation reaction or an alkylation reaction, resulting in attachment of one or more PEG moieties via acyl or alkyl groups. In certain embodiments, PEG moieties are attached to a polypeptide through the α- or ε-amino group of one or more amino acids, although any other points of attachment known in the art are also contemplated.

Pegylation by acylation typically involves reacting an activated ester derivative of a PEG moiety with a polypeptide. A non-limiting exemplary activated PEG ester is PEG esterified to N-hydroxysuccinimide (NHS). As used herein, acylation is contemplated to include, without limitation, the following types of linkages between a polypeptide and PEG: amide, carbamate, and urethane. See, e.g., Chamow, *Bioconjugate Chem.*, 5:133-140 (1994). Pegylation by alkylation typically involves reacting a terminal aldehyde derivative of a PEG moiety with a polypeptide in the presence of a reducing agent. Non-limiting exemplary reactive PEG aldehydes include PEG propionaldehyde, which is water stable, and mono C1-C10 alkoxy or aryloxy derivatives thereof. See, e.g., U.S. Pat. No. 5,252,714.

In certain embodiments, a pegylation reaction results in poly-pegylated polypeptides. In certain embodiments, a pegylation reaction results in mono-, di-, and/or tri-pegylated polypeptides. Further, desired pegylated species may be separated from a mixture containing other pegylated species and/or unreacted starting materials using various purification techniques known in the art, including among others, dialysis, salting-out, ultrafiltration, ion-exchange chromatography, gel filtration chromatography, and electrophoresis.

Exemplary Attachment of Fusion Partners

The fusion partner may be attached, either covalently or non-covalently, to the amino-terminus or the carboxy-terminus of an FGFR3 ECD. The attachment may also occur at a location within the FGFR3 ECD other than the amino-terminus or the carboxy-terminus, for example, through an amino acid side chain (such as, for example, the side chain of cysteine, lysine, histidine, serine, or threonine).

In either covalent or non-covalent attachment embodiments, a linker may be included between the fusion partner and the FGFR3 ECD. Such linkers may be comprised of amino acids and/or chemical moieties.

Exemplary methods of covalently attaching a fusion partner to an FGFR3 ECD include, but are not limited to, translation of the fusion partner and the FGFR3 ECD as a single amino acid sequence and chemical attachment of the fusion partner to the FGFR3 ECD. When the fusion partner and the FGFR3 ECD are translated as single amino acid sequence, additional amino acids may be included between the fusion partner and the FGFR3 ECD as a linker. In certain embodiments, the linker is glycine-serine ("GS"). In certain embodiments, the linker is selected based on the polynucleotide sequence that encodes it, to facilitate cloning the fusion partner and/or FGFR3 ECD into a single expression construct (for example, a polynucleotide containing a particular restriction site may be placed between the polynucleotide encoding the fusion partner and the polynucleotide encoding the FGFR3 ECD, wherein the polynucleotide containing the restriction site encodes a short amino acid linker sequence).

When the fusion partner and the FGFR3 ECD are covalently coupled by chemical means, linkers of various sizes can typically be included during the coupling reaction.

Exemplary methods of non-covalently attaching a fusion partner to an FGFR3 ECD include, but are not limited to, attachment through a binding pair. Exemplary binding pairs include, but are not limited to, biotin and avidin or streptavidin, an antibody and its antigen, etc. The selected non-covalent attachment method should be suitable for the conditions under which the FGFR3 ECD fusion molecule will be used, taking into account, for example, the pH, salt concentrations, and temperature.

Non-Human FGFR3 ECDs

As described above, in certain embodiments, the FGFR3 ECD amino acid sequence is that of a non-human mammal. In such embodiments, the FGFR3 ECD sequence may be derived from mammals including, but not limited to, rodents, simians, felines, canines, equines, bovines, porcines, ovines, caprines, mammalian laboratory animals, mammalian farm animals, mammalian sport animals, and mammalian pets. Known non-human FGFR3 ECD sequences include those with GenBank Accession Nos. NP_001156687, NP_001156688, NP_001156689, NP_445881, NP_990840, and NP_776743. As set forth above, such FGFR3 ECD sequences can be modified in the same way as the human FGFR3 ECD sequences described above. In other words, non-human FGFR3 ECDs include the corresponding native FGFR3 ECDs, FGFR3 ECD variants, FGFR3 ECD fragments, native FGFR3 ECD fragments, variants of FGFR3 ECD fragments, FGFR3 ECD acidic region muteins, FGFR3 ECD D1-D2 linker chimeras, FGFR3 ECD glycosylation mutants, and FGFR3 ECD fusion molecules.

Nucleic Acid Molecules, Vectors, and Protein Expression Methods

Nucleic acid molecules that encode FGFR3 ECDs can be constructed by one skilled in the art using recombinant DNA techniques conventional in the art.

In certain embodiments, a polynucleotide encoding a polypeptide of the invention comprises a nucleotide sequence that encodes a signal peptide, which, when translated, is fused to the amino-terminus of the FGFR3 polypeptide. As discussed above, the signal peptide may be the native signal peptide, the signal peptide of FGFR1, FGFR2, FGFR3, or FGFR4, or may be another heterologous signal peptide. The amino acid sequences for certain exemplary FGFR signal peptides are shown, e.g., in SEQ ID NOs: 16 to 18. Certain exemplary signal peptides are known in the art, and are described, e.g., in the online Signal Peptide Database maintained by the Department of Biochemistry, National University of Singapore, http://proline.bic.nus.edu.sg/spdb/index.html (see also Choo et al., *BMC Bioinformatics*, 6: 249 (2005)); and in PCT Publication No. WO 2006/081430.

To prepare the polypeptides, the nucleic acid molecule comprising the polynucleotide encoding the FGFR3 ECD may be placed into a vector suitable for expression in a selected host cell. Such vectors include, but are not limited to, DNA vectors, phage vectors, viral vectors, retroviral vectors, etc.

In certain embodiments, a vector is selected that is optimized for expression of polypeptides in CHO-S or CHO-S-derived cells. Exemplary such vectors are described, e.g., in Running Deer et al., *Biotechnol. Prog.* 20:880-889 (2004).

In certain embodiments, a vector is chosen for in vivo expression of the polypeptides of the invention in animals, including humans. In certain such embodiments, expression of the polypeptide is under the control of a promoter that functions in a tissue-specific manner. For example, liver-specific promoters are described, e.g., in PCT Publication No, WO 2006/076288.

The polypeptides of the invention can be expressed, in various embodiments, in prokaryotic cells, such as bacterial cells; or eukaryotic cells, such as fungal cells, plant cells, insect cells, and mammalian cells. Such expression may be carried out, for example, according to procedures known in the art. Certain exemplary eukaryotic cells that can be used to express polypeptides include, but are not limited to, Cos cells, including Cos 7 cells; 293 cells, including 293-6E and 293-T cells; CHO cells, including CHO-S and DG44 cells; and NS0 cells. In certain embodiments, a particular eukaryotic host cell is selected based on its ability to make certain desired post-translational modifications of the polypeptide of the invention. For example, in certain embodiments, CHO cells produce FGFR3 ECDs that have a higher level of glycosylation and/or sialylation than the same polypeptide produced in 293 cells.

Introduction of a nucleic acid into a desired host cell can be accomplished by any method known in the art, including, but not limited to, calcium phosphate transfection, DEAE-dextran mediated transfection, cationic lipid-mediated transfection, electroporation, transduction, infection, etc. Certain exemplary methods are described, e.g., in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to methods known in the art.

In certain embodiments, a polypeptide can be produced in vivo in an animal that has been engineered or transfected with a nucleic acid molecule encoding the polypeptide, according to methods known in the art.

Purification of FGFR3 ECD Polypeptides

The polypeptides of the invention can be purified by various methods known in the art. Such methods include, but are not limited to, the use of affinity matrices, ion exchange chromatography, and/or hydrophobic interaction chromatography. Suitable affinity ligands include any ligands of the FGFR3 ECD, antibodies to FGFR3 ECD, or, in the case of an FGFR3 ECD fusion, a ligand of the fusion partner. For example, a Protein A, Protein G, Protein A/G, or an antibody affinity column may be used to bind to an Fc fusion partner to purify a polypeptide of the invention. Hydrophobic interactive chromatography, for example, a butyl or phenyl column, may also suitable for purifying certain polypeptides.

Methods of Administration

Routes of Administration and Carriers

The polypeptides of the invention can be administered in vivo by various routes known in the art, including, but not limited to, intravenous, subcutaneous, parenteral, intranasal, intramuscular, buccal, intraperitoneal, intradermal, topical, transdermal, and intrathecal, or otherwise by implantation or inhalation. The subject compositions can be formulated into preparations in solid, semi-solid, liquid, or gaseous forms; including, but not limited to, tablets, capsules, powders, granules, ointments, solutions, injections, inhalants, and aerosols. Nucleic acid molecules encoding the polypeptides of the invention can be coated onto gold microparticles and delivered intradermally by a particle bombardment device, or "gene gun," as described in the literature (see, e.g., Tang et al., *Nature* 356:152-154 (1992)).

In some embodiments, compositions comprising the polypeptides of the invention are provided in formulation with pharmaceutically acceptable carriers, a wide variety of which are known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7$^{th}$ ed., Lippincott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, carriers, and diluents, are available to the public. Moreover, various pharmaceutically acceptable auxiliary substances, such as pH adjusting and buffering agents, tonicity adjusting agents, stabilizers, wetting agents and the like, are also available to the public. Certain non-limiting exemplary carriers include saline, buffered saline, dextrose, water, glycerol, ethanol, and combinations thereof.

In various embodiments, compositions comprising polypeptides of the invention can be formulated for injection by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of the polypeptides of the invention are also provided. In certain embodiments, a unit dosage is provided wherein the unit dosage contains a predetermined amount of a composition comprising a polypeptide of the invention, with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that can be reconstituted upon addition of an appropriate liquid, for example, sterile water. In certain embodiments, the composition comprises one or more substances that inhibit protein aggregation, including, but not limited to, sucrose and arginine. In certain embodiments, a composition of the invention comprises heparin and/or a proteoglycan.

The FGFR3 ECD compositions are administered in an amount effective to promote hair growth. The effective amount is typically dependent on the weight of the subject being treated, his or her physical or health condition, the extensiveness of the condition to be treated, and/or the age of the subject being treated. In general, the polypeptides of the invention can be administered subcutaneously in an amount in the range of about 10 ng to about 500 µg. Optionally, the polypeptides of the invention can be administered subcutaneously in an amount in the range of about 10 ng to about 100 µg. Further optionally, the polypeptides of the invention can be administered subcutaneously in an amount in the range of about 10 ng to about 10 µg. In general, the polypeptides of the invention can be administered intravenously in an amount in the range of about 10 µg/kg body weight to about 30 mg/kg body weight per dose. Optionally, the polypeptides of the invention can be administered intravenously in an amount in the range of about 100 μg/kg body weight to about 20 mg/kg body weight per dose. Further optionally, the polypeptides of the invention can be administered intravenously in an amount in the range of about 0.5 mg/kg body weight to about 20 mg/kg body weight per dose The compositions comprising the polypeptides of the invention can be administered as needed to subjects. Determination of the frequency of administration can be made by persons skilled in the art, such as an attending physician or pharmacist or hair growth specialist based on considerations of the condition being treated, age of the subject being treated, severity of the condition being treated, general state of health of the subject being treated and the like. In certain embodiments, an effective dose of the polypeptide of the invention is administered to a subject one or more times. In various embodiments, an effective dose of the polypeptide of the invention is administered to the subject no more than once a year, nor more than twice a year, no more than twice a month, no more than once a week, no more than twice a week, or no more than three times a week. In various embodiments, an effective dose of the polypeptide of the invention is administered to the subject for no more than a week, for no more than a month, for no more than three months, for no more than six months, or for no more than a year.

Combination Therapy

Polypeptides of the invention may be administered alone or with other modes of treatment. They may be provided before, substantially contemporaneous with, or after other modes of treatment. Certain exemplary combination therapies could include a combination of an FGFR3 ECD with minoxidil, finasteride, dutasteride, other 5-alpha reductase inhibitors, and/or hair transplant surgery.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of an FGFR3 ECD-Fc Fusion Molecule

An FGFR3 ECD-Fc having a 3 amino acid carboxy-terminal deletion from the FGFR3-IIIc ECD ("FGFR3 ECD Δ3-Fc" or "FGFR3 ECD-Fc") fused to Fc with a GS linker (SEQ ID NO: 33) was subcloned into the pTT5 and pDEF38 vectors using PCR and conventional subcloning techniques.

The primary sequence and domain structure of the FGFR3 ECD moiety in the FGFR3 ECD Δ3-Fc construct is shown in FIG. 1. FIG. 2 shows an amino acid sequence alignment of a portion of the C-terminal region of FGFR ECDs, denoting Ig domain III.

For transient expression in 293-6E cells, the vector pTT5 (Biotechnology Research Institute, Montreal, Canada) was used. For expression of the fusion proteins in CHO-S host cells, we used the pTT5 and pDEF38 (ICOS Corporation, Bothell, Wash.) vectors. DG44 (Invitrogen, Carlsbad, Calif.) is a derivative cell line of the CHO-S cell line that we have found can give higher yields of recombinant proteins. For expression of the fusion proteins in DG44 host cells, we used the vector pDEF38.

Example 2

Purification of Expressed Protein

An FGFR3 ECD-Fc fusion protein expressed from recombinant host cells was purified from the cell culture supernatant using a first purification step of Protein-A affinity chromatography, followed by a second purification step of butyl hydrophobic interaction chromatography. For the Protein-A affinity chromatography step, the components of the media were separated on a Mabselect Protein-A Sepharose column (GE Healthcare Bio-Sciences, Piscataway, N.J.), which will bind to the Fc region of the fusion molecule. The column was equilibrated with ten column volumes of a sterile buffer of 10 mM Tris, 100 mM NaCl, pH 8.0; then the cell culture supernatant was applied to the column. The column was washed with eight column volumes of sterile 10 mM Tris, 100 mM NaCl buffer, pH 8.0. The bound material, including the fusion protein, was then eluted at a rate of 10 ml/min with a one step elution using seven column volumes of elution buffer (100 mM glycine, 100 mM NaCl, pH 2.7). Ten ml fractions were collected in tubes containing one ml 1 M Tris pH 8.0 (Ambion, Austin, Tex.) to neutralize the eluate. Fractions comprising the fusion protein were identified by gel electrophoresis and pooled.

For the second purification step of butyl hydrophobic interaction chromatography, pooled Protein-A column eluates were further purification on a butyl Sepharose column using a GE Healthcare Akta Purifier 100 (GE Healthcare Bio-Sciences, Piscataway, N.J.). The column was first equilibrated with five column volumes of sterile 10 mM Tris, 1 M ammonium sulfate, pH 8.0. A half volume of 3 M ammonium sulfate was then added to the eluate, which was then applied to the equilibrated butyl Sepharose column. The column was washed with four column volumes of the equilibration buffer and the bound material was eluted at a rate of five ml/min with a linear gradient starting at 50% equilibration buffer/50% elution buffer (10 mM Tris pH 8.0) and ending at 90% elution buffer/10% equilibration buffer over a total volume of 20 column volumes. Finally, an additional two column volumes of 100% elution buffer was used. Fourteen ml fractions were collected. The fusion protein was eluted with approximately 40-60% elution buffer. The fractions containing the bulk of the fusion protein were identified by gel electrophoresis and pooled.

After purification, endotoxin levels were checked by the limulus amoebocyte lysate (LAL) assay (Cambrex, Walkersville, Md.). Endotoxin levels were confirmed to be less than or equal to 1 endotoxin unit (EU) per mg of the fusion protein.

Example 3

Transient Expression of Fusion Protein in CHO-S Host Cells

An FGFR3 ECD-Fc fusion protein was transiently expressed in CHO-S cells. Briefly, a 500 ml culture of CHO-S cells (Invitrogen) was established by inoculating $0.5 \times 10^6$ cells/ml in fresh 37° C. Freestyle CHO medium containing 8 mM L-Glutamine (Invitrogen). The cells were grown in a 2 l plastic flask and were derived from a seed strain that was continuously maintained up to passage 20. The following day, the cells were counted and diluted, if necessary, to $1\times10^6$ cells/ml in 37° C. Freestyle CHO medium (Invitrogen) with a cell viability greater than 95%. The cells were transfected by transferring 10 ml of 37° C. OptiPRO SFM medium containing 8 mM L-Glutamine (dilution media) into two 50 ml tubes. To the first tube (A), 625 ul of FreestyleMax transfection reagent (Invitrogen) were added. To the second tube (B), 625 ug of DNA were added. Both tubes were gently mixed by inverting, and the contents of tube A were immediately added to tube B, followed by gentle mixing by inversion. The mixture was incubated at room temperature for between 10 to 20 mM, and was then delivered drop-wise into the 500 ml cell culture in the 2 l culture flask while slowly swirling the flask. The culture was then transferred to an incubator at 37° C., 5% $CO_2$, 125 rpm. After six days, the cell viability was greater than 80%, and the culture supernatant was collected into a centrifuge bottle. The supernatant was centrifuged at 1,000×g for 10 min, transferred to a new centrifuge bottle, and centrifuged at 4,000×g for 10 mM. The supernatant was collected into a new bottle and filtered through a 0.2 um filter. The supernatant was stored at 37° C. prior to the purification step. The fusion protein was purified from the culture supernatant as described in Example 2, except that Q Sepharose anion exchange chromatography was used as the second purification step. Protein-A eluates were applied to a Q Sepharose HP column (GE Healthcare 17-1014-01) equilibrated with five column volumes of sterile buffer (10 mM Tris, 50 mM NaCl, pH 8.0). The column was washed with five column volumes of the same buffer and the bound material was eluted at a rate of five ml/min with a linear gradient of 15 column volumes of elution buffer (10 mM Tris, 2 M NaCl, pH 8.0), followed by five column volumes with 100% elution buffer. Fourteen ml fractions were collected and the fractions comprising the FGFR3 ECD-Fc were identified by gel electrophoresis and pooled. The FGFR3 ECD-Fc fusion proteins eluted with approximately 10-25% elution buffer. Protein levels were determined based on absorbance measurements at 280 nm.

Example 4

Stable Production in DG44 Cells

The expression vector FGFR3-Fc/pDEF38, described in Example 1, was used to transfect DG44 host cells for stable production of FGFR ECD fusion proteins. The untransfected DHFR-negative CHO cell line, DG44, was cultured in CHO-CD serum free medium (Irvine Scientific, Irvine, Calif.) supplemented with 8 mM L-Glutamine, 1× Hypoxanthine/Thymidine (HT; Invitrogen), and 18 ml/L of Pluronic-68 (Invitrogen). About 50 ug of plasmid DNA of each of FGFR3 ECD-Fc/pDEF38, FGFR2 ECD-Fc/pDEF38, and ABmut1/pDEF38 was linearized by digestion with restriction enzyme PvuI, then precipitated by addition of ethanol, briefly air-dried, and then resuspended in 400 ul of sterile, distilled water. The DG44 cells were seeded into a shaker flask at a density of about $4\times10^5$/ml the day before transfection, and reached a density of about $0.8\times10^6$/ml on the day of transfection. The cells were harvested by centrifugation and about $1\times10^7$ cells were used per transfection.

For transfection, each cell pellet was resuspended in 0.1 ml of Nucleofector V solution and transferred to an Amaxa Nucleofector cuvette (Amaxa, Cologne, Germany). About 5 ug of the resuspended linearized plasmid DNA was added and mixed with the suspended DG44 cells in the cuvette. Cells were then electroporated with an Amaxa Nucleofector Device II using program U-024. Electroporated cells were cultured in CHO-CD medium for two days and then transferred into selective medium (CHO-CD serum free medium supplemented with 8 mM L-Glutamine and 18 ml/L Pluronic-68). The selective medium was changed once every week. After about 12 days, 1 ug/ml R3 Long IGF I growth factor (Sigma, St. Louis, Mo.) was added to the medium and the culture was continued for another week until confluent. The supernatants from pools of stably transfected cell lines were assayed by a sandwich ELISA to determine the product titer. This transfection method generated an expression level of about 30 ug/ml of the expressed fusion protein from the pools of stably transfected cells.

Example 5

Specificity and Affinity of Ligand Binding to FGFR3-IIIc ECD-Fc Measured by Biacore Analysis The specificity of FGF ligand binding to an FGFR3-IIIc ECD-Fc (SEQ ID NO: 10) was assessed using Biacore® T100 surface plasmon resonance (SPR) technology (Biacore; Piscataway, N.J.). Expression constructs for expressing the FGFR3-IIIc ECD-Fc (SEQ ID NO: 10) fusion protein in 293-6E host cells using the pTT5 vector were made in a manner similar to that described above using cDNAs prepared internally and conventional techniques. The FGFR3-IIIc ECD-Fc fusion protein was produced from 293-6E host cells as described in WO/2007/014123 (PCT/US06/028597) (Examples 2 and 3).

Protein-A was covalently linked to a CM5 chip, according to manufacturer's instructions and then an FGFR ECD fusion protein was bound to the chip by the interaction of the Fc domain with the Protein-A. The FGF ligands were placed in contact with the FGFR ECD fusion protein, also according to manufacturer's instructions, in the presence of HBS-P buffer (Biacore; Piscataway, N.J.) supplemented with 50 ug/ml heparin (Sigma; St. Louis, Mo.).

All the recombinant FGF ligands were from R&D Systems (Minneapolis, Minn.) except for FGF-18 which was from Wako Chemicals (Richmond, Va.). FGF ligands were each tested at six to eight concentrations ranging from 4.5 ng/ml to 10 ug/ml. The FGF ligands were recombinant and of human origin, except for FGF-18, which was of recombinant mouse origin.

The binding of the FGFR3-IIIc ECD-Fc, to various FGF ligands was measured in real time. Table 1 below shows the resulting association constants ($k_a$), dissociation constants ($k_d$) and equilibrium dissociation constants ($K_D$) that were determined from these studies.

As summarized in Table 1, the relative rank of FGF binding affinity to the FGFR3-IIIc-Fc was FGF-18>FGF-1>FGF-9>FGF-2, FGF-4>FGF-20>FGF-5>FGF-7>FGF-19.

TABLE 1

Real-Time Ligand Binding to FGFs

| | FGFR3-IIIc-ECD-Fc | | |
|---|---|---|---|
| Ligand | $k_a$ (l/(M * s)) | $k_d$ (l/s) | $K_D$ (M) |
| FGF-1 | $2.83 \times 10^6$ * | $3.31 \times 10^{-4}$ * | $1.26 \times 10^{-10}$* |
| FGF-2 | $3.36 \times 10^5$ | $1.37 \times 10^{-3}$ | $1.06 \times 10^{-9}$ |
| FGF-4 | $8.08 \times 10^5$ | $1.55 \times 10^{-3}$ | $1.91 \times 10^{-9}$ |
| FGF-5 | $2.31 \times 10^5$ | $1.69 \times 10^{-3}$ | $9.70 \times 10^{-9}$ |
| FGF-7 | $3.19 \times 10^5$ | $4.71 \times 10^{-2}$ | $1.48 \times 10^{-7}$ |
| FGF-9 | $7.76 \times 10^5$ | $4.17 \times 10^{-4}$ | $5.37 \times 10^{-10}$ |
| FGF-18 | $5.16 \times 10^6$ * | $1.80 \times 10^{-4}$ * | $3.50 \times 10^{-11}$ * |
| FGF-19 | $5.63 \times 10^4$ | $4.43 \times 10^{-1}$ | $7.87 \times 10^{-6}$ |
| FGF-20 | $1.85 \times 10^5$ | $4.04 \times 10^{-4}$ | $2.17 \times 10^{-9}$ |

* = average of two independent measurements

Example 6

Systemic Delivery of an FGFR3 ECD Fusion Molecule Promotes Hair Growth in Mice Eight-week-old female C57B1.6 mice (Charles River Labs, Wilmington, Mass.) were weighed and sorted into 4 treatment groups of 5 or 10 mice each based on body weight, as shown in Table 2. All mice were shaved on the right flank. Group I was dosed IV with 0.2 cc/mouse saline and groups 2-4 were dosed IV with 20 mg/kg of the appropriate test article in a 0.2 cc/mouse volume as indicated in Table 2.

TABLE 2

Study Design of Hair Growth in Wildtype Mice

| Study Group | Dose Group | Sequence |
|---|---|---|
| 1 | Saline | — |
| 2 | FGFR2-ECD-Fc | SEQ ID NO: 32 |
| 3 | FGFR3-ECD-Fc | SEQ ID NO: 33 |
| 4 | FGFR4-ECD-Fc (ABMut1) | SEQ ID NO: 31 |

Figure 3B:
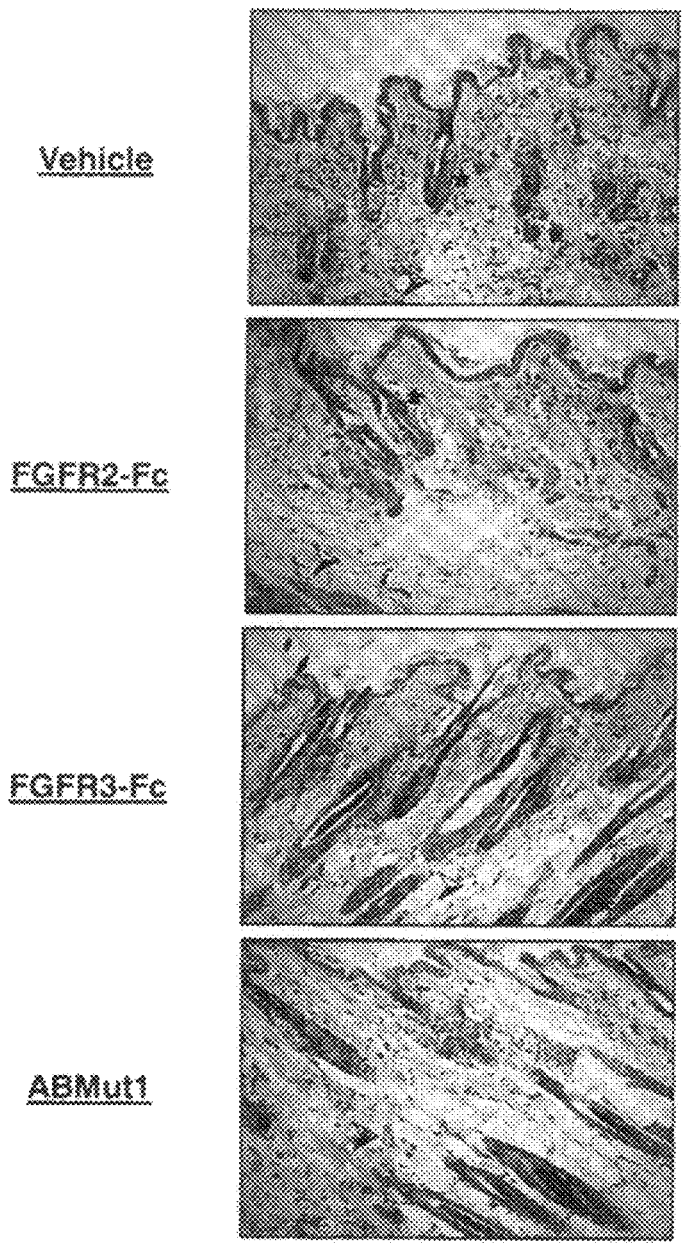
FIG. 3B shows that systemic delivery of an FGFR3 ECD-Fc (SEQ ID NO: 33) and ABMut1 (SEQ ID NO: 31, an FGFR4 ECD variant-Fc) induces anagen in hair follicles of eight-week-old mice. Shown are paraffin-embedded skin biopsies stained with Haematoxylin/Eosin from mice treated with vehicle, the FGFR3 ECD-Fc, an FGFR2 ECD-Fc or ABMut1 at days 14 post-dose. By day 14, mice treated with the FGFR3 ECD-Fc or ABMut1 showed an elongation of the dermal papilla (*) into the fatty layer of the dermis (➢), showing that a single dose of the FGFR3 ECD-Fc or ABMut1 can induce anagen (the growth phase of the hair cycle).

On day 14 post initial dose, animals were observed for hair growth. As shown in FIG. 3A, marked hair growth was observed in 4 of 5 animals in group 3 (FGFR3-ECD-Fc) and 2 of 5 animals in group 4 (FGFR4-ECD-Rc; ABMut1) compared to the control group 1 (Saline) as indicated by pigmented skin and partial hair regrowth. There was no observable hair growth in group 2 (FGFR2-ECD-Fc).

The animals were euthanized on the same day and a 2 cm² skin biopsy was harvested and fixed in neutral buffered saline for 12 hours. Samples were paraffin embedded and structural differences were visualized with Haematoxylin/Eosin staining (Gladstone Institute Histology Core, San Francisco, Calif.). Structural differences were observed in animals from groups 3 and 4 as demonstrated by elongation of the dermal papilla (*) into the fatty layer of the dermis ( ▶ ) (FIG. 3B), suggesting re-entry into the anagen or growth phase of the hair cycle.

Example 7

An FGFR3 ECD Fusion Molecule Promotes Hair Growth in Mice in a Dose Dependent Manner At exactly 61 days of age, female C57B1.6 mice (Charles River Labs, Wilmington, Mass.) were weighed and sorted into 7 groups of 10 mice each as demonstrated in the chart below. The entire back and belly of all mice was shaved and the animals were dosed subcutaneously with 0.1 mg/kg, 1 mg/kg or 10 mg/kg of FGFR3-ECD-Fc in a 0.05 cc volume directly in the center of the belly along the midline according to the chart below.

TABLE 3

Study Design of Hair Growth at Increasing Doses

| Group | Dose Group | Dose (mg/kg) | N |
|---|---|---|---|
| 1 | Vehicle | 0 | 10 |
| 2 | FGFR3-ECD-Fc | 0.1 | 10 |
| 3 | FGFR3-ECD-Fc | 1 | 10 |
| 4 | FGFR3-ECD-Fc | 10 | 10 |

On Day 13 post initial dose, mice were euthanized, and the area of skin that was shaved on day 0 was removed (pelt), tacked down flat and photographed. Photographs of mouse pelts were analyzed for hair growth using Image J (National Institutes of Health, Bethesda, Md.). Hair growth was calculated by measuring the percentage area of hair re-growth within a given pelt per total area of the pelt. As shown in FIG. 4, marked hair growth was observed in groups 3 and 4 compared to group 1. Additionally, significantly more hair growth was observed in groups 3 and 4 compared to group 2 and in group 4 compared to group 3, demonstrating that FGFR3-ECD-Fc stimulated hair growth in a dose dependent manner. FIG. 4 represents the average percentage of hair growth per dose group.

INDUSTRIAL APPLICABILITY

The FGFR ECDs described herein can be used to promote hair growth, which may be useful to subjects suffering from hair loss.

TABLE OF SEQUENCES

Table 4 provides certain sequences discussed herein. Solely for the sake of simplicity and not for any limiting reason, all FGFR sequences are shown without the signal peptide unless otherwise indicated.

TABLE 4

Sequences and Descriptions

| SEQ. ID. NO | Description | Sequence |
|---|---|---|
| 1 | FGFR3 IIIc | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERWDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV YAGILSYGVG FFLFILVVAA VTLCRLRSPP KKGLGSPTVH KISRFPLKRQ VSLESNASMS SNTPLVRIAR LSSGEGPTLA NVSELRLPAD PKWELSRARL TLGKPLGEGC FGQVVMAEAI GIDKDRAAKP VTVAVKMLKD DATDKDLSDL VSEMEMMKMI GKHKNIINLL GACTQGGPLY VLVEYAAKGN LREFLRARRP PGLDYSFDTC KPPEEQLTFK DLVSCAYQVA RGMEYLASQK CIHRDLAARN |

TABLE 4-continued

Sequences and Descriptions

| SEQ. ID. NO | Description | Sequence |
|---|---|---|
| | | VLVTEDNVMK IADFGLARDV HNLDYYKKTT NGRLPVKWMA PEALFDRVYT HQSDVWSFGV LLWEIFTLGG SPYPGIPVEE LFKLLKEGHR MDKPANCTHD LYMIMRECWH AAPSQRPTFK QLVEDLDRVL TVTSTDEYLD LSAPFEQYSP GGQDTPSSSS SGDDSVFAHD LLPPAPPSSG GSRT |
| 2 | FGFR3 Δ8-10 | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKVS LESNASMSSN TPLVRIARLS SGEGPTLANV SELELPADPK WELSRARLTL GKPLGEGCFG QVVMAEAIGI DKDRAAKPVT VAVKMLKDDA TDKDLSDLVS EMEMMKMIGK HKNIINLLGA CTQGGPLTVL VEYAAKGNLR EFLRARRPPG LDYSFDTCKP PEEQLTFKDL VSCAYQVARG MEYLASQKCI HRDLAARNVL VTEDNVMKIA DFGLARDVHN LDYYKKTTNG RLPVKWMAPE ALFDRVYTHQ SDVWSFGVLL WEIFTLGGSP YPGIPVEELF KLLKEGHRMD KPANCTHDLY MIMRECWHAA PSQRPTFKQL VEDLDRVLTV TSTDEYLDLS APFEQYSPGG QDTPSSSSSG DDSVFAHDLL PPAPPSSGGS RT |
| 3 | FGFR3 IIIb | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG RRFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKSW ISESVEADVR LRLANVSERD GGEYLCRATN FIGVAEKAFW LSVHGPRAAE EELVEADEAG SVYAGILSYG VGFFLFILVV AAVTLCRLRS PPKKGLGSPT VHKISRFPLK RQVSLESNAS MSSNTPLVRI ARLSSGEGPT LANVSELELP ADPKWELSRA RLTLGKPLGE GCFGQVVMAE AIGIDKDRAA KPVTVAVKML KDDATDKDLS DLVSEMEMMK MIGKHKNIIN LLGACTQGGP LYVLVEYAAK GNLREFLRAR RPPGLDYSFD TCKPPEEQLT FKDLVSCAYQ VARGMEYLAS QKCIHRDLAA RNVLVTEDNV MKIADFGLAR DVHNLDYYKK TTNGRLPVYW MAPEALFDRV YTHQSDVWSF GVLLWEIFTL GGSPYPGIPV EELFKLLKEG HRMDKPANCT HDLYMIMREC WHAAPSQRPT FKQLVEDLDR VLTVTSTDEY LDLSAPFEQY SPGGQDTPSS SSSGDDSVFA HDLLPPAPPS SGGSRT |
| 4 | FGFR3-IIIb ECD | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKSW ISESVEADVR LRLANVSERD GGEYLCRATN FIGVAEKAFW LSVHGPRAAE EELVEADEAG SVYAG |
| 5 | FGFR3-IIIc ECD | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV YAG |
| 6 | FGFR3-Δ8-10 ECD | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLK |

TABLE 4-continued

Sequences and Descriptions

| SEQ. ID. NO | Description | Sequence |
|---|---|---|
| 7 | FGFR3-IIIb ECD + Fc | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKSW ISESVEADVR LRLANVSERD GGEYLCRATN FIGVAEKAFW LSVHGPRAAE EELVEADEAG SVYAGEPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 8 | FGFR3-IIIb ECD + GS linker + Fc | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKSW ISESVEADVR LRLANVSERD GGEYLCRATN FIGVAEKAFW LSVHGPRAAE EELVEADEAG SVYAGGSEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 9 | FGFR3-IIIc ECD + Fc | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV YAGEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 10 | FGFR3-IIIc ECD + GS linker + Fc | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV YAGGSEPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 11 | FGFR3-IIIc ECD + Fc (R3Mut1) (FGFR3-IIIc ECD with C-terminal deletion of VYAG, fused to Fc) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSE PKSSDKTHTC PPCPAPELLG GPSVFLFPPK PKDTLMISRT PEVTCVVVDV |

TABLE 4-continued

Sequences and Descriptions

| SEQ. ID. NO | Description | Sequence |
|---|---|---|
| | | SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 12 | FGFR3-IIIc ECD + Fc (R3Mut2) (FGFR3-IIIc ECD with C-terminal deletion of EAGSVYAG, fused to Fc) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 13 | FGFR3-IIIc ECD + Fc (R3Mut3) (FGFR3-IIIc ECD with C-terminal deletion of DEAGSVYAG, fused to Fc) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCRVYSDAQ PHIQWLKHVE VNGSKVGPDG TPYVTVLKTA GANTTDKELE VLSLHNVTFE DAGEYTCLAG NSIGFSHHSA WLVVLPAEEE LVEAEPKSSD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 14 | FGFR3-IIIc ECD + Fc (R3Mut4) (FGFR3-IIIc ECD with C-terminal deletion of LVEADEAGSVYAG, fused to Fc) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSTRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 15 | FGFR3-IIIc ECD + Fc (R3Mut5) (FGFR3-IIIc ECD with C-terminal deletion of VLPAEEELVEADE AGSVYAG, fused to Fc) | ESLGTEQRVV GRAAEVPGPE FGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |

TABLE 4-continued

Sequences and Descriptions

| SEQ. ID. NO | Description | Sequence |
|---|---|---|
| 16 | Fc C237S (GI17939658_233-464_C237S) | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 17 | Fc (GI34528298_241-468) | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 18 | Fc (GI19684073_245-473) | ESKYGPPCPS CPAPEFLGGP SVFLFPPKPK DTLMISRTPE VTCVVVDVSQ EDPEVQFNWY VDGVEVENAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 19 | FGFR1 signal peptide | MWSWKCLLFWAVLVTATLCTA |
| 20 | FGFR2 signal pepide | MVSWGRFICLVVVTMATLSLA |
| 21 | FGFR3 signal peptide | MGAPACALALCVAVAIVAGASS |
| 22 | FGFR4 signal peptide | MRLLLALLGILLSVPGPPVLS |
| 23 | FGFR3 D1-D2 linker | DAPSSGDDED GEDEAEDTGV DTG |
| 24 | FGFR3 acid box region 1 | DDEDGED |
| 25 | FGFR3 acid box region 2 | DDEDGEDE |
| 26 | FGFR3 acid box region 3 | DDEDGEDEAE |
| 27 | FGFR3 acid box region4 | DDEDGEDEAED |
| 28 | FGFR3-IIIc ECD R3(110-117): R1(105-112) + Fc (FGFR3-IIIc ECD D1-D2 linker chimera fused to Fc) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSE DDDDDDDEAE DTGVDTGAPY WTRPERMDLK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV YAGEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 29 | FGFR3-IIIc ECD with signal peptide | MGAPACALAL CVAVAIVAGA SSESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH FSVRVTDAPS SGDDEDGEDE AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE EELVEADEAG SVYAG |

TABLE 4-continued

Sequences and Descriptions

| SEQ. ID. NO | Description | Sequence |
|---|---|---|
| 30 | FGFR3-IIIc ECD Δ3 (FGFR3-IIIc ECD with a deletion of the C-terminal 3 amino acids YAG) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV |
| 31 | FGFR4 ECD Δ17 R1 D1-D2 linker chimera + Fc (also called FGFR4 ECD (ABMut1: delta 17)-Fc and ABMut1) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVLGSDVE LLCKVYSDAQ PHIQWLKHIV INGSSFGADG FPYVQVLKTA DINSSEVEVL YLRNVSAEDA GEYTCLAGNS IGLSYQSAWL TVLPEPKSSD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 32 | FGFR2 ECD Δ3 + GS linker + Fc | RPSFSLVEDT TLEPEEPPTK YQISQPEVYV AAPGESLEVR CLLKDAAVIS WTKDGVHLGP NNRTVLIGEY LQIKGATPRD SGLYACTASR TVDSETWYFM VNVTDAISSG DDEDDTDGAE DFVSENSNNK RAPYWTNTEK MEKRLHAVPA ANTVKFRCPA GGNPMPTMRW LKNGKEFKQE HRIGGYKVRN QHWSLIMESV VPSDKGNYTC VVENEYGSIN HTYHLDVVER SPHRPILQAG LPANASTVVG GDVEFVCKVY SDAQPHIQWI KHVEKNGSKY GPDGLPYLKV LKAAGVNTTD KEIEVLYIRN VTFEDAGEYT CLAGNSIGIS FHSAWLTVLP APGREKEITA SPDGSEPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 33 | FGFR3-IIIc ECD Δ3 + GS linker + Fc (FGFR3-IIIc ECD with a deletion of the C-terminal 3 amino acids YAG, fused to Fc with a GS linker) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSG DDEDGEDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 34 | FGFR3-IIIc ECD R3(110-117): R1(105-112) (FGFR3-IIIc ECD D1-D2 linker chimera) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSE DDDDDDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV YAG |
| 35 | FGFR3-IIIc ECD Δ3 R3(110-117): R1(105-112) + Fc (FGFR3-IIIc ECD D1-D2 linker | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSE DDDDDDEAE DTGVDTGAPY WTRPERMDKK LLAVPAANTV RFRCPAAGNP TPSISWLKNG REFRGEHRIG GIKLRHQQWS LVMESVVPSD |

TABLE 4-continued

Sequences and Descriptions

| SEQ. ID. NO | Description | Sequence |
|---|---|---|
| | chimera with a deletion of the C-terminal three amino acids YAG, fused to Fc) | RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 36 | FGFR3-IIIc ECD Δ3 R3(110-117): R1(105-112): (FGFR3-IIIc ECD D1-D2 linker chimera with a deletion of the C-terminal three amino acids YAG) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSE DDDDDDDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV |
| 37 | FGFR3-IIIc ECD Δ3 R3(110-117): R1(105-112) + GS linker + Fc (FGFR3-IIIc ECD D1-D2 linker chimera with a deletion of the C-terminal three amino acids YAG, fused to Fc with a GS linker) (also called FGFR3ECD(FGFR3 (110-117): FGFR1(105-112): delta3)-GS linker-Fc and R3(110-117): R1(105-112)) | ESLGTEQRVV GRAAEVPGPE PGQQEQLVFG SGDAVELSCP PPGGGPMGPT VWVKDGTGLV PSERVLVGPQ RLQVLNASHE DSGAYSCRQR LTQRVLCHFS VRVTDAPSSE DDDDDDDEAE DTGVDTGAPY WTRPERMDKK LLAVPAANTV RFRCPAAGNP TPSISWLKNG REFRGEHRIG GIKLRHQQWS LVMESVVPSD RGNYTCVVEN KFGSIRQTYT LDVLERSPHR PILQAGLPAN QTAVLGSDVE FHCKVYSDAQ PHIQWLKHVE VNGSKVGPDG TPYVTVLKTA GANTTDKELE VLSLHNVTFE DAGEYTCLAG NSIGFSHHSA WLVVLPAEEE LVEADEAGSV GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 38 | FGFR4 D1-D2 linker | DSLTSSNDDED PKSHRDPSNR HSYPQQ |
| 39 | FGFR1 D1-D2 linker | DALPSSEDDDD DDDSSSEEKE TDNTKPNPV |
| 40 | FGFR2 D1-D2 linker | DAISSGDDED DTDGAEDFVS ENSNNKR |
| 41 | FGFR3 acid box | DDEDGE |
| 42 | FGFR3 long acid box | GDDEDGEDEA ED |
| 43 | FGFR3 short acid box | DDED |

The invention claimed is:

1. A method of promoting hair growth comprising administering a fibroblast growth factor receptor 3 extracellular domain (FGFR3 ECD) to a subject in need thereof in an amount sufficient to promote hair growth.

2. The method of claim 1, wherein the FGFR3 ECD is a native FGFR3 ECD.

3. The method of claim 1, wherein the FGFR3 ECD is an FGFR3 ECD splice variant.

4. The method of claim 1, wherein the FGFR3 ECD is an FGFR3 ECD fragment.

5. The method of claim 1, wherein the FGFR3 ECD is a native FGFR3 ECD fragment.

6. The method of claim 1, wherein the FGFR3 ECD is a variant of an FGFR3 ECD fragment.

7. The method of claim 1, 2, 4, or 5, wherein the FGFR3 ECD is chosen from FGFR3-Δ8-10 ECD, FGFR3-IIIb ECD, and FGFR3-IIIc ECD.

8. The method of claim 1, wherein the FGFR3 ECD is an FGFR3 ECD acidic region mutein.

9. The method of claim 1, wherein the FGFR3 ECD is an FGFR3 ECD D1-D2 linker chimera.

10. The method of claim 1, wherein the FGFR3 ECD is an FGFR3 ECD glycosylation mutant.

11. The method of claim 1, wherein the amino acid sequence of the FGFR3 ECD is at least 80% identical to SEQ ID NO: 4, 5, 6, or 30.

12. The method of claim 1, wherein the amino acid sequence of the FGFR3 ECD is at least 85% identical to SEQ ID NO: 4, 5, 6, or 30.

13. The method of claim 1, wherein the amino acid sequence of the FGFR3 ECD is at least 90% identical to SEQ ID NO: 4, 5, 6, or 30.

14. The method of claim 1, wherein the amino acid sequence of the FGFR3 ECD is at least 95% identical to SEQ ID NO: 4, 5, 6, or 30.

15. The method of claim 1, wherein the amino acid sequence of the FGFR3 ECD is at least 99% identical to SEQ ID NO: 4, 5, 6, or 30.

16. The method of claim 1, wherein the amino acid sequence of the FGFR3 ECD comprises the amino acid sequence of SEQ ID NO: 30.

17. The method of claim 1, wherein the FGFR3 ECD lacks a signal sequence.

18. The method of claim 1, wherein the FGFR3 ECD comprises a signal sequence.

19. The method of claim 18, wherein the signal sequence is the native signal sequence of FGFR1, FGFR2, FGFR3, or FGFR4.

20. The method of claim 1, wherein the subject is a rodent, simian, human, feline, canine, equine, bovine, porcine, ovine, caprine, mammalian laboratory animal, mammalian farm animal, mammalian sport animal, or mammalian pet.

21. The method of claim 20, wherein the subject is a human.

22. The method of claim 1, wherein the administering is intravenous, subcutaneous, intraperitoneal, topical, transdermal, or intradermal.

23. A method of promoting hair growth comprising administering a fibroblast growth factor receptor 3 extracellular domain (FGFR3 ECD) fusion molecule to a subject in need thereof in an amount sufficient to promote hair growth.

24. The method of claim 23, wherein the FGFR3 ECD fusion molecule comprises an FGFR3 ECD polypeptide and a fusion partner.

25. The method of claim 23, wherein the FGFR3 ECD polypeptide is a native FGFR3 ECD.

26. The method of claim 23, wherein the FGFR3 ECD polypeptide is an FGFR3 ECD splice variant.

27. The method of claim 23, wherein the FGFR3 ECD polypeptide is an FGFR3 ECD fragment.

28. The method of claim 23, wherein the FGFR3 ECD polypeptide is a variant of an FGFR3 ECD fragment.

29. The method of claim 23, 24, 25, or 27 wherein the FGFR3 ECD polypeptide is chosen from FGFR3-Δ8-10 ECD, FGFR3-IIIb ECD, and FGFR3-IIIc ECD.

30. The method of claim 23, wherein the FGFR3 ECD polypeptide is an FGFR3 ECD acidic region mutein.

31. The method of claim 23, wherein the FGFR3 ECD polypeptide is an FGFR3 ECD D1-D2 linker chimera.

32. The method of claim 23, wherein the FGFR3 ECD polypeptide is an FGFR3 ECD glycosylation mutant.

33. The method of claim 23, wherein the fusion partner is selected from an Fc, albumin, and polyethylene glycol.

34. The method of claim 24, wherein the fusion partner is an Fc.

35. The method of claim 23, wherein the FGFR3 ECD fusion molecule has the amino acid sequence of SEQ ID NO: 33.

36. The method of claim 23, wherein the FGFR3 ECD fusion molecule lacks a signal sequence.

37. The method of claim 23, wherein the FGFR3 ECD fusion molecule comprises a signal sequence.

38. The method of claim 23, wherein the signal sequence is the native signal sequence of FGFR1, FGFR2, FGFR3, or FGFR4.

39. The method of claim 23, wherein the subject is a rodent, simian, human, feline, canine, equine, bovine, porcine, ovine, caprine, mammalian laboratory animal, mammalian farm animal, mammalian sport animal, or mammalian pet.

40. The method of claim 39, wherein the subject is a human.

41. The method of claim 23, wherein the administering is intravenous, subcutaneous, intraperitoneal, topical, transdermal, or intradermal.

* * * * *